US009017672B2

(12) United States Patent
Yu et al.

(10) Patent No.: US 9,017,672 B2
(45) Date of Patent: Apr. 28, 2015

(54) HEXON TAT-PTD MODIFIED ADENOVIRUS AND USES THEREOF

(71) Applicants:Di Yu, Uppsala (SE); Magnus Essand, Uppsala (SE)

(72) Inventors: Di Yu, Uppsala (SE); Magnus Essand, Uppsala (SE)

(73) Assignee: Immunicum Aktiebolag, Gothenburg (SE)

( * ) Notice: Subject to any disclaimer, the term of this patent is extended or adjusted under 35 U.S.C. 154(b) by 0 days.

(21) Appl. No.: 13/892,789

(22) Filed: May 13, 2013

(65) Prior Publication Data

US 2013/0302313 A1 Nov. 14, 2013

Related U.S. Application Data

(60) Provisional application No. 61/645,666, filed on May 11, 2012, provisional application No. 61/705,729, filed on Sep. 26, 2012.

(51) Int. Cl.

| | | |
|---|---|---|
| *C12N 15/87* | (2006.01) |
| *A61K 48/00* | (2006.01) |
| *A61K 35/76* | (2006.01) |
| *A61K 45/06* | (2006.01) |
| *A61K 38/16* | (2006.01) |
| *C07K 14/005* | (2006.01) |
| *C12N 15/86* | (2006.01) |

(52) U.S. Cl.
CPC ............ *C12N 15/87* (2013.01); *A61K 48/0058* (2013.01); *A61K 35/761* (2013.01); *A61K 45/06* (2013.01); *A61K 38/164* (2013.01); *C07K 14/005* (2013.01); *C12N 15/86* (2013.01); *C07K 2319/10* (2013.01); *C12N 2710/10322* (2013.01); *C12N 2710/10332* (2013.01); *C12N 2710/10345* (2013.01); *C12N 2810/6054* (2013.01); *C12N 2830/008* (2013.01)

(58) Field of Classification Search
CPC .................. A61K 35/761; C12N 2710/10322; C12N 2710/10345
See application file for complete search history.

(56) References Cited

U.S. PATENT DOCUMENTS

| | | | |
|---|---|---|---|
| 7,001,596 | B1 | 2/2006 | Johnson et al. |
| 7,048,920 | B2 | 5/2006 | Yu et al. |
| 7,078,030 | B2 | 7/2006 | Johnson et al. |
| 7,396,679 | B2 | 7/2008 | Johnson et al. |
| 7,951,585 | B2 | 5/2011 | Ke |

OTHER PUBLICATIONS

Yu et al. J. Virol. 2011; 85(24): 13114-13123 (published online Sep. 28, 2011).*
Kurachi et al (Gene Therapy. 2007; 14: 1160-1165).*
Kurachi al (Gene Therapy. 2007; 14: 266-274).*
Eguchi et al (J. Biol. Chem. 2001; 276: 26204-26210).*
Raki et al (Gene Therapy. 2005; 12: 1198-1205).*
Zhang et al (Journal of Expermiental & Clinical Cancer Research. 2010; 29(52): 1-7).*
Roberts et al (Nature. May 2006; 441: 239-243).*
Amedeo Amedei et al., The neutrophil-activating protein of *Helicobacter pylori* promotes Th1 immune responses, The Journal of Clinical Investigation, 2006, pp. 1092-1101, vol. 116, No. 4.
Bjorn Carlsson et al., Ex vivo stimulation of cytomegalovirus (CMV)-specific T cells using CMV pp65-modified dendritic cells as stimulators, British Journal of Haematology, 2003, pp. 428-438, vol. 121, Blackwell Publishing Ltd.
W.S. Cheng et al., An oncolytic conditionally replicating adenovirus for hormone-dependent and hormone-independent independent prostate cancer, Cancer Gene Therapy, 2006, pp. 13-20, vol. 13, Nature Publishing Group.
A. Danielsson et al, Increased therapeutic efficacy of the prostate-specific oncolytic adenovirus Ad[I/PPT-E1A] by reduction of the insulator size and introduction of the full-length E3 region, Cancer Gene Therapy, 2008, pp. 203-213 vol. 15, Nature Publishing Group.
M. Essand, Oncolytic Viruses for the Treatment of Neuroendocrine Tumors, Horm Metab Res, 2011, pp. 877-883, vol. 43, Georg Thieme Verlag KG Stuttgart, New York.
Yusuke Eto et al., Transduction of adenovirus vectors modified with cell-penetrating peptides, Peptides, 2009, pp. 1548-1552, vol. 30, Elsevier.
Juan Fueyo et al., A mutant oncolytic adenovirus targeting the Rb pathway produces anti-glioma effect in vivo, Oncogene, 2000, pp. 2-12, vol. 19, Macmillan Publishers Ltd.
S. Kurachi et al., Fiber-modified adenovirus vectors containing the TAT peptide derived from HIV-1 in the fiber knob have efficient gene transfer activity, Gene Therapy, 2007, pp. 1160-1165, vol. 14.
Young Sook Lee et al., Enhanced Antitumor Effect of Oncolytic Adenovirus Expressing Interleukin-12 and B7-1 in an Immunocompetent Murine Model, Clinical Cancer Research, 2006, pp. 5859-5868, vol. 12, No. 19, American Association for Cancer Research.
Justyna Leja et al., Double-Detargeted Oncolytic Adenovirus Shows Replication Arrest in Liver Cells and Retains Neuroendocrine Cell Killing Ability, PLoS ONE, 2010, pp. 1-9, vol. 5, No. 1.
J. Leja et al., Oncolytic adenovirus modified with somatostatin motifs for selective infection of neuroendocrine tumor cells, Gene Therapy, 2011, pp. 1052-1062, vol. 18, Macmillan Publishers Limited.
Siobhan NI Choileain and Anne L Astier, CD46 processing: A means of expression, Immunobiology, 2012, pp. 169-175, vol. 217, Elsevier GmbH.
Nilsson et al., Development of an adenoviral vector system with adenovirus serotype 35 tropism; efficient transient gene transfer into primary malignant hematopoietic cells, The Journal of Gene Medicine, 2004, pp. 631-641, vol. 6, Wiley InterScience.
Jian Qiao et al., Purging metastases in lymphoid organs using a combination of antigen-nonspecific adoptive T cell therapy, oncolytic virotherapy and immunotherapy, Nature Medicine, 2008, pp. 37-44, vol. 14, No. 1, Nature Publishing Group.
Johan Rebetz et al., Fiber Mediated Receptor Masking in Non-Infected Bystander Cells Restricts Adenovirus Cell Killing Effect but Promotes Adenovirus Host Co-Existence, PLoS ONE, 2009, pp. 1-13, vol. 4, No. 12.
Barbara Satin et al., The Neutrophil-activating Protein (HP-NAP) of *Helicobacter pylori* Is a Protective Antigen and a Major Virulence Factor, J. Exp. Med., 2000, pp. 1467-1476, vol. 191, No. 9, The Rockefeller University Press.

(Continued)

*Primary Examiner* — Scott Long
(74) *Attorney, Agent, or Firm* — Browdy and Neimark, PLLC

(57) ABSTRACT

The invention provides a hexon Tat-PTD modified adenovirus, a gene delivery vector based on the modified adenovirus that enhances gene delivery efficiency, and an oncolytic agent based on the modified adenovirus that enhances tumor cell killing efficiency and improves therapeutic outcome.

24 Claims, 25 Drawing Sheets

(56) References Cited

OTHER PUBLICATIONS

Figure 3:
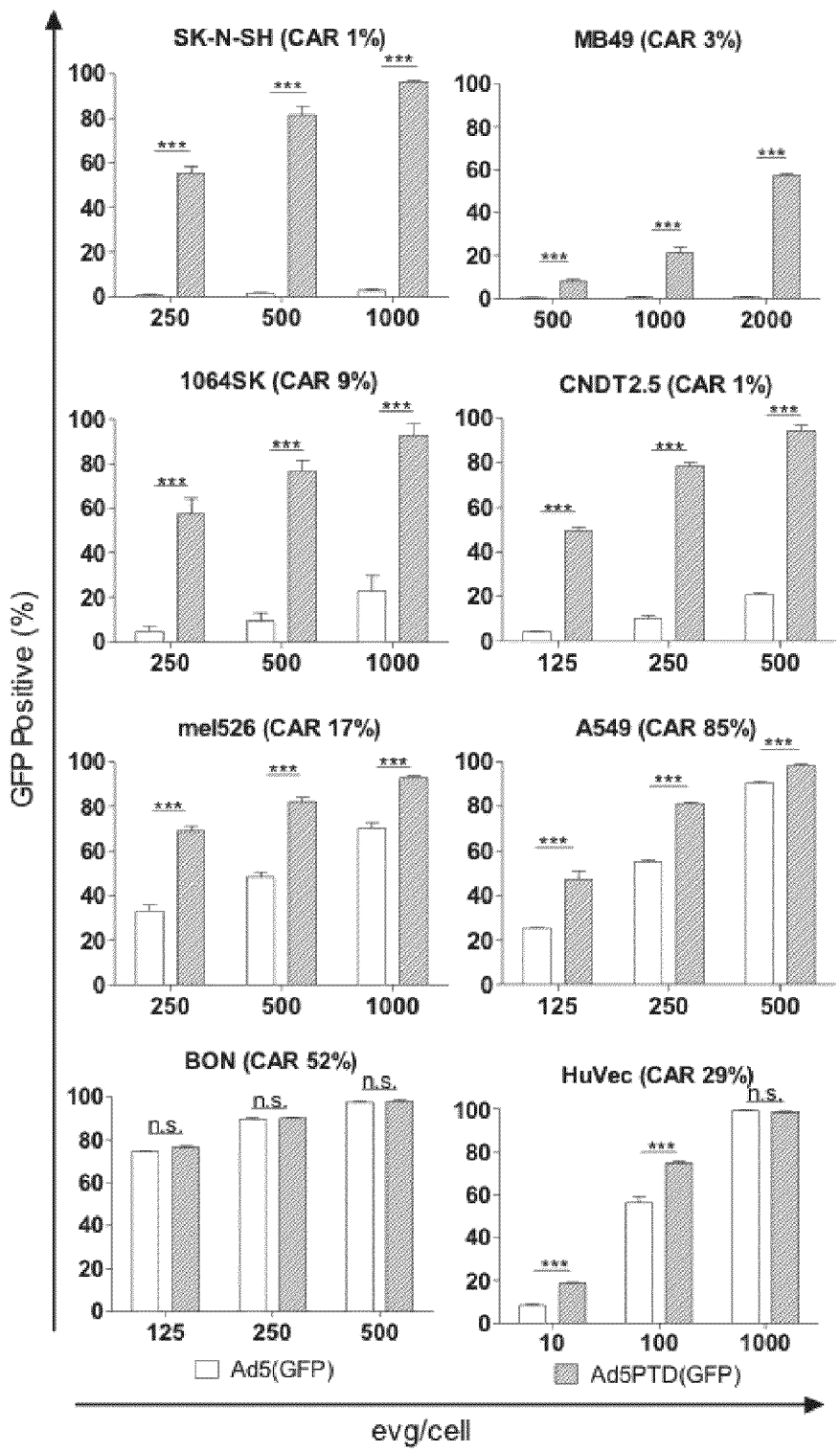

Rupa Sawant and Vladimir Torchilin et al., Intracellular transduction using cell-penetrating peptides, Molecular BioSystems, 2010, pp. 628-640, vol. 6, Royal Society of Chemistry.

Richard J. Stanton et al., Re-engineering adenovirus vector systems to enable high-throughput analyses of gene function, BioTechniques, 2008, pp. 659-668, vol. 45, No. 6.

Shuji Terao et al., Improved Gene Transfer into Renal Carcinoma Cells Using Adenovirus Vector Containing RGD Motif, Anticancer Research, 2009, pp. 2997-3002, vol. 29.

Eric Vives et al., A Truncated HIV-1 Tat Protein Basic Domain RapidlyTranslocates through the Plasma Membrane and Accumulates in the Cell Nucleus, The Journal of Biological Chemistry, 1997, pp. 16010-16017, vol. 272, No. 25, The American Society for Biochemistry and Molecular Biology, Inc.

Hongjie Wang et al., Desmoglein 2 is a receptor for adenovirus serotypes 3, 7, 11 and 14, Nature Medicine, 2011, pp. 96-105, vol. 17, No. 1, Nature America, Inc.

Wang Yu and Hu Fang et al., Clinical Trials with Oncolytic Adenovirus in China, Current Cancer Drug Targets, 2007, pp. 659-670, vol. 7, Bentham Science Publishers Ltd.

* cited by examiner

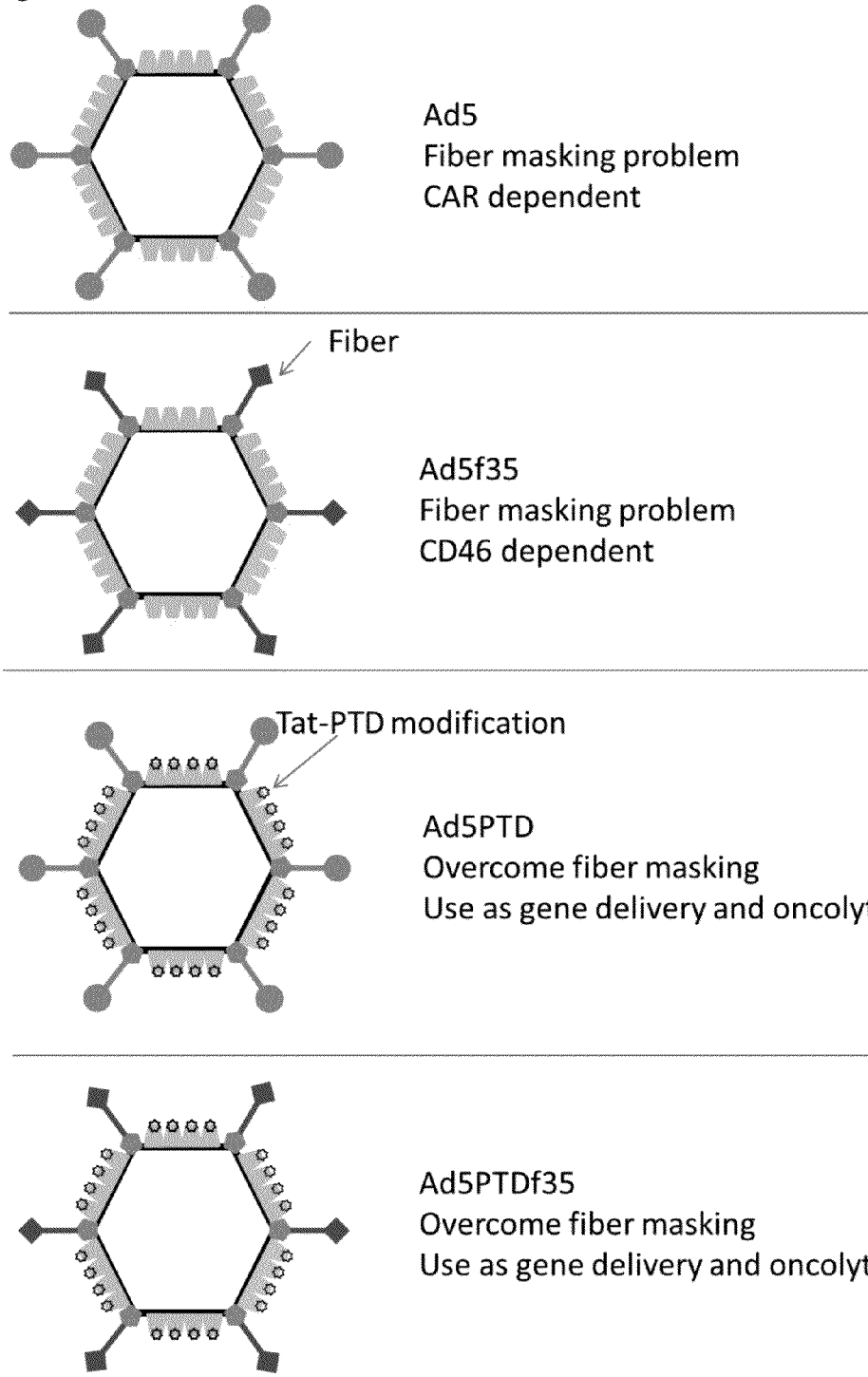

Figure 2

```
MATPSMMPQWSYMHISGQDASEYLSPGLVQFARATETYFSLNNKFRNPTVAPT
HDVTTDRSQRLTLRFIPVDREDTAYSYKARFTLAVGDNRVLDMASTYFDIRGV
LDRGPTFKPYSGTAYNALAPKGAPNPCEWDEAATALEINLEEEDDDNEDEVDE
QAEQQKTHVFGQAPYSGINITKEGIQIGVEGQTPKYADKTFQPEPQIGESQWY
ETEINHAAGRVLKKTTPMKPCYGSYAKPTNENGGQGILVKQQNGKLESQVEMQ
FFSTTAGGGAGGGYGRKKRRQRRRGGGAGGGATPKVVLYSEDVDIETPDTHIS
YMPTIKEGNSRELMGQQSMPNRPNYIAFRDNFIGLMYYNSTGNMGVLAGQASQ
LNAVVDLQDRNTELSYQLLLDSIGDRTRYFSMWNQAVDSYDPDVRIIENHGTE
DELPNYCFPLGGVINTETLTKVKPKTGQENGWEKDATEFSDKNEIRVGNNFAM
EINLNANLWRNFLYSNIALYLPDKLKYSPSNVKISDNPNTYDYMNKRVVAPGL
VDCYINLGARWSLDYMDNVNPFNHHRNAGLRYRSMLLGNGRYVPFHIQVPQKF
FAIKNLLLLPGSYTYEWNFRKDVNMVLQSSLGNDLRVDGASIKFDSICLYATF
FPMAHNTASTLEAMLRNDTNDQSFNDYLSAANMLYPIPANATNVPISIPSRNW
AAFRGWAFTRLKTKETPSLGSGYDPYYTYSGSIPYLDGTFYLNHTFKKVAITF
DSSVSWPGNDRLLTPNEFEIKRSVDGEGYNVAQCNMTKDWFLVQMLANYNIGY
QGFYIPESYKDRMYSFFRNFQPMSRQVVDDTKYKDYQQVGILHQHNNSGFVGY
LAPTMREGQAYPANFPYPLIGKTAVDSITQKKFLCDRTLWRIPFSSNFMSMGA
LTDLGQNLLYANSAHALDMTFEVDPMDEPTLLYVLFEVFDVVRVHRPHRGVIE
TVYLRTPFSAGNATT
```

Figure 7

Table 1. List of primers used in this study

| Primer name | Sequences (5'-3') |
|---|---|
| pF.Shuni | GATTTGGCCATTTTCGCGGG |
| pR.Shuni | GGCGGCTGCTGCAAAACAGAT |
| pF.HVR5-als | AATGGAAAGCTAGAAAGTCAAGTGGAAATGCAATTTTCCC<u>TGTGACGGAAGATCACTTCG</u> |
| pR.HVR5-als | CCACTTTAGGAGTCAAGTTATCAC AdmCD40L Ad5PTDf35(mCD40L)
PTD= Protein Transduction Domain

HEXON TAT-PTD MODIFIED ADENOVIRUS AND USES THEREOF

TECHNICAL FIELD

The present invention generally refers to a hexon Tat-PTD modified adenovirus and uses thereof.

BACKGROUND

Adenovirus serotype 5 (Ad5), which belongs to the C group of human adenoviruses, has been widely used as an oncolytic agent for cancer therapy [1]. Various Ad5 viruses have shown considerable therapeutic effects and have been extensively evaluated in animal models and clinical trials [2]. Their advantage in cancer therapy is due to the self-propagation properties that involve replication in and lysis of infected tumor cells, which leads to secondary infection and killing of adjacent cells within the tumor. A number of therapeutic approaches relying upon adenovirus have been envisioned, including adenoviral vectors expressing therapeutic genes, oncolytic adenoviruses under control of different promoters, which have been described in U.S. Pat. No. 7,951,585, U.S. Pat. No. 7,396,679, U.S. Pat. No. 7,048,920, U.S. Pat. No. 7,078,030 and U.S. Pat. No. 7,001,596, included herein by reference.

One factor limiting the efficacy of Ad5 in cancer therapy is that Ad5 infection is dependent on coxsackievirus-adenovirus receptor (CAR) expression on target cells. CAR is an adhesion molecule expressed in tight-junctions and many cancer cells down-regulate CAR expression, which results in difficulties in achieving sufficient infection and, as a consequence, the oncolytic therapeutic effect is hampered [3]. One approach to circumvent this is to genetically modify Ad5 and use fibers or fiber knobs from the B group of adenoviruses, which do not bind to CAR but to other cell surface receptors [4]. A second limiting factor is fiber-masking of receptors. This is caused by overproduction of adenovirus fiber proteins [5], which are released from the infected cell before cell lysis. The released fibers bind to CAR on non-infected neighboring cells, thereby limiting infection efficiency of progeny virus [5]. The fiber-masking problem is not limited to the Ad5 fiber but has also been observed for the Ad35 fiber, which binds to CD46 [5]. These limitations must be overcome to develop successful oncolytic adenovirus agents.

Cell penetrating peptides (CPPs) are short (usually <30aa) peptides with ability to penetrate tissues or enter cells at a relatively high efficiency. In some cases, members of linear CPPs have the "carrier" features that transport the conjugated "cargos" (from small molecules to large DNA complexes) into cells. Hereafter, CPPs were referred to the class with carrier features unless mentioned specifically. The first insight on cellular uptake of CPPs was discovered in 1965, when researchers reported that histones and basic poly-amino acids stimulate the uptake of albumin by tumor cells in culture. Although the transactivator of transcription (TAT) from HIV-1 virus was the first CPP investigated to determine whether it could function as a carrier, it was not until 1994 that the carrier/penetrating properties of these peptides were fully acknowledged. Further studies by Lebleu's group revealed that the ability to penetrate plasma membranes was associated with certain domains of the TAT protein, which was designated the protein transduction domains (PTD) [6]. Since then an increasing number of new CPPs have been found and characterized. However, the mechanism of uptake is still not fully elucidated, which became the biggest limitation for their transition into clinical applications. Different models have been proposed to explain the penetration into cells. They can be mainly divided into energy-dependent endocytosis and direct translocation via the lipid bilayer. There is also another report suggesting that CPPs only play a role in "adherence" or "docking" to the cell surface while endocytosis mediates the actual cellular uptake. The secondary structure was also found to be important for different classes of CPPs.

SUMMARY

The present invention provides a hexon Tat-PTD modified adenovirus (designated: Ad5PTD or Ad5PTDf35) and the uses thereof.

In one embodiment of the present invention, there is provided an Ad5PTD-based or Ad5PTDf35-based gene delivery vector, wherein the vector enhances the gene delivery efficiency.

In another embodiment of the present invention, there is provided an Ad5PTD-based or Ad5PTDf35-based oncolytic agent, wherein the agent enhances the tumor cell killing efficiency and thereby improves the therapeutic outcome.

In another embodiment of the present invention, there is provided an Ad5PTD-based or Ad5PTDf35-based oncolytic agent, wherein the agent(s) is armed with therapeutic gene(s) to further enhances the tumor cell killing efficiency and thereby further improves the therapeutic outcome.

In another embodiment of the present invention, there is provided an Ad5PTD-based or Ad5PTDf35-based oncolytic agent, wherein the agent(s) replication ability is controlled by a tissue-specific or tumor-specific promoter, to enhance the selectivity of the agent(s) cell killing efficiency and thereby further improves the therapeutic outcome.

In yet another embodiment of the present invention, there is provided an Ad5PTD-based or Ad5PTDf35-based oncolytic agent wherein the agent overcomes the fiber-masking problem and thereby improves the therapeutic outcome.

The invention is further defined in the claims.

The invention offers the following advantages:
Provide enhanced transduction level of adenoviruses and adenoviral vectors for both CAR-negative and CAR-positive cells.
Provide enhanced killing efficacy for adenoviruses of CAR-negative and CAR-positive cells.
Provide oncolytic adenoviruses, which overcome the fiber-masking problem caused by overproduction of fiber molecules in the viral replication cycle.

Other advantages offered by the present invention will be appreciated upon reading of the following description of the embodiments of the invention.

SHORT DESCRIPTION OF THE DRAWINGS

The invention together with further objects and advantages thereof, may best be understood by making reference to the following description taken together with the accompanying drawings, in which:

FIG. 1 is a schematic illustration of a native human adenovirus serotype 5 (Ad5); an Ad5 with the fiber from adenovirus serotype 35 (Ad5f35); an Ad5 with a Tat-PTD sequence in hexon hypervariable region 5 (Ad5PTD); an Ad5 with both fiber 35 and Tat-PTD modifications (Ad5PTDf35).

FIG. 2 is the sequence of Tat-PTD modified adenovirus 5 hexon. The linker sequences are underlined. The Tat-PTD sequence is in bold.

FIG. 3 shows the transduction of Ad5PTD-based adenoviral vector in both CAR-negative cells and CAR-positive cells.

Cells were transduced in suspension for 2 hours with GFP-expressing adenoviral vectors at various evg/cell. The viral vector was then washed away and the cells were analyzed by flow cytometry 48 hours after transduction. Values are shown as mean±SD from three independent experiments, each with triplicate samples. Unpaired Student's t-test was used for comparison (\*\*\*: p<0.001; not significant (n.s.): p>0.05; n=3). The values in parenthesis after each cell line name indicate the CAR expression level (percentage of CAR positive cells) as assessed by FACS staining.

Figure 4:
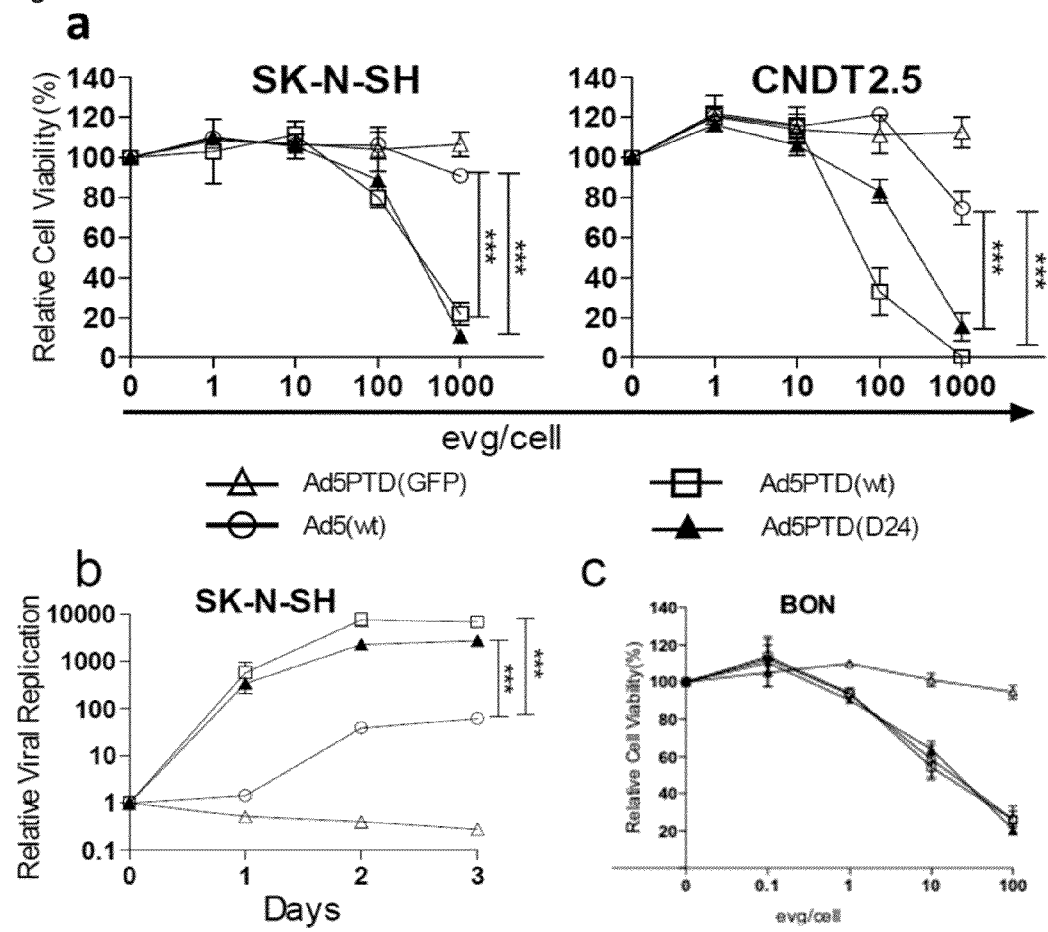

FIG. 4 shows the Ad5PTD-based adenoviruses yield enhanced cell killing and replication activities. (a) A neuroblastoma (SK-N-SH) and a neuroendocrine tumor (CNDT2.5) cell line, both with low CAR expression, or (c) a neuroendocrine cell line (BON) with high expression level of CAR, was transduced with Ad5PTD-based or wild type virus at various evg/cell. The replication-deficient viral vector Ad5PTD(GFP) was used as a negative control. The relative cell viability was analyzed 4 days after transduction by MTS assay. Data are shown as mean±SD from three independent experiments, each with triplicate samples (\*\*\*: p<0.001; n=3). (b) Neuroblastoma (SK-N-SH) cells were transduced with virus at 500 evg/cell. Viral genomic DNA was isolated at day 0, 1, 2, 3 after transduction and quantified using real-time PCR. Values show the fold change in relation to day 0 (set to 1). Data is shown as mean±SD from three independent experiments, each with triplicate samples (\*\*\*: p<0.001; n=3).

Figure 5:
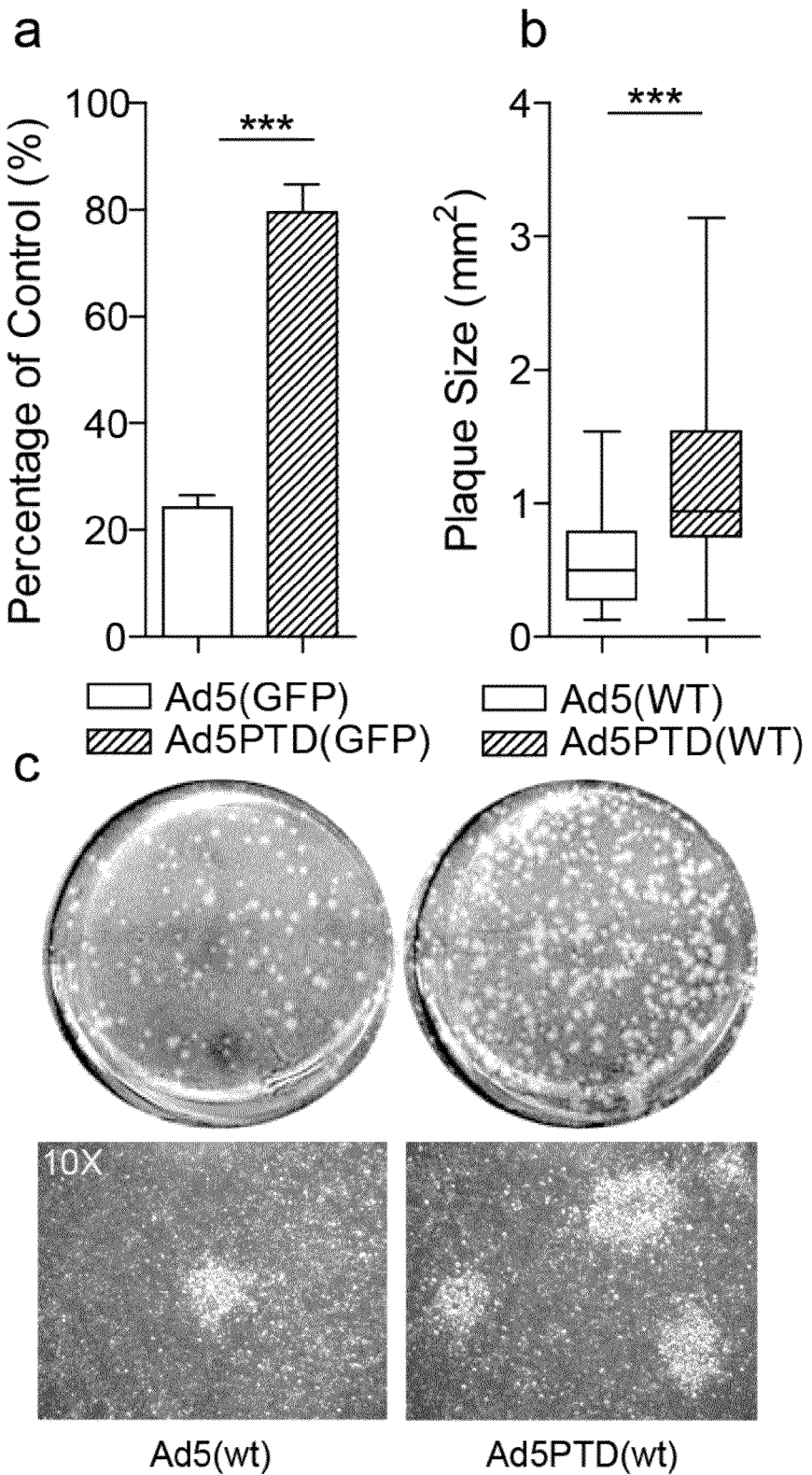

FIG. 5 shows that the Ad5PTD-based adenoviruses overcome the fiber-masking problem and spreads more efficiently than a non-modified virus. (a) A549 cells were transduced with GFP-expressing adenoviral vectors at 500 evg/cell in the presence of free soluble Ad5 fiber molecules and analyzed by flow cytometry after 2 days. Transduced cells in the absence of soluble Ad5 fiber served as control (set to 100%) (\*\*\*: p<0.001; n=3). (b) Monolayer A549 cells were transduced with equal amount of either Ad5(wt) or Ad5PTD(wt) followed by low-melting agar overlay and neutral red staining. Plaque sizes measured after 8 days are represented as whisker box-plot with median, lower quartile, upper quartile, minimum and maximum values. Comparison was performed by the non-parametric Mann-Whitney test (\*\*\*: p<0.001, n=50). (c) Representative images of the whole well from the plaque formation assay at day 8, formed by Ad5(wt) and Ad5PTD(wt). 10× magnification pictures were shown accordingly as well.

Figure 6:
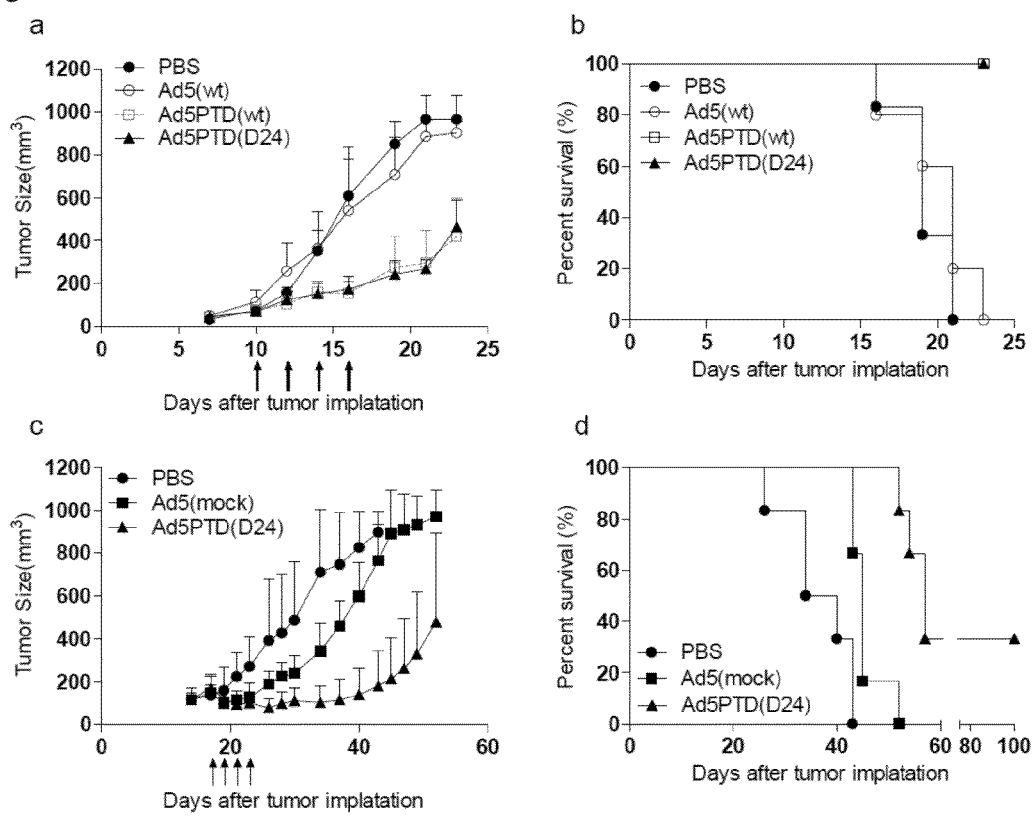

FIG. 6 shows the tumor growth inhibition of Ad5PTD-based adenovirus treatments on tumor-bearing Nude and SCID/beige mice models. It also shows the survival of tumor-bearing Nude and SCID/beige mice treated with Ad5PTD-based adenoviruses. (a) SCID/beige mice harboring subcutaneous neuroblastoma, SK-N-SH, were treated by peritumoral virus injections as indicated by the arrows. (c) NMRI-nude mice harboring subcutaneous neuroendocrine tumor, CNDT2.5, were treated by intratumoral virus injections as indicated by arrows. The tumor volume was monitored by caliper measurements. Six mice per group were used and data is shown as mean±SD. Mice were sacrificed when the tumor size reached 800 mm$^3$. The experiment of SCID/beige mice was terminated when the last mouse in the Ad5(wt)-treatment group was sacrificed due to wounds on the tumors. The experiment of NMRI-nude was terminated at day 100 after tumor implantation. A Kaplan-Meier survival curve shows survival data (b, SCID/beige mice; d, NMRI-nude mice). Log-rank test was performed for comparison.

FIG. 7 shows the primers used in this invention to generate Ad5PTD-based vectors/viruses.

Figure 8:
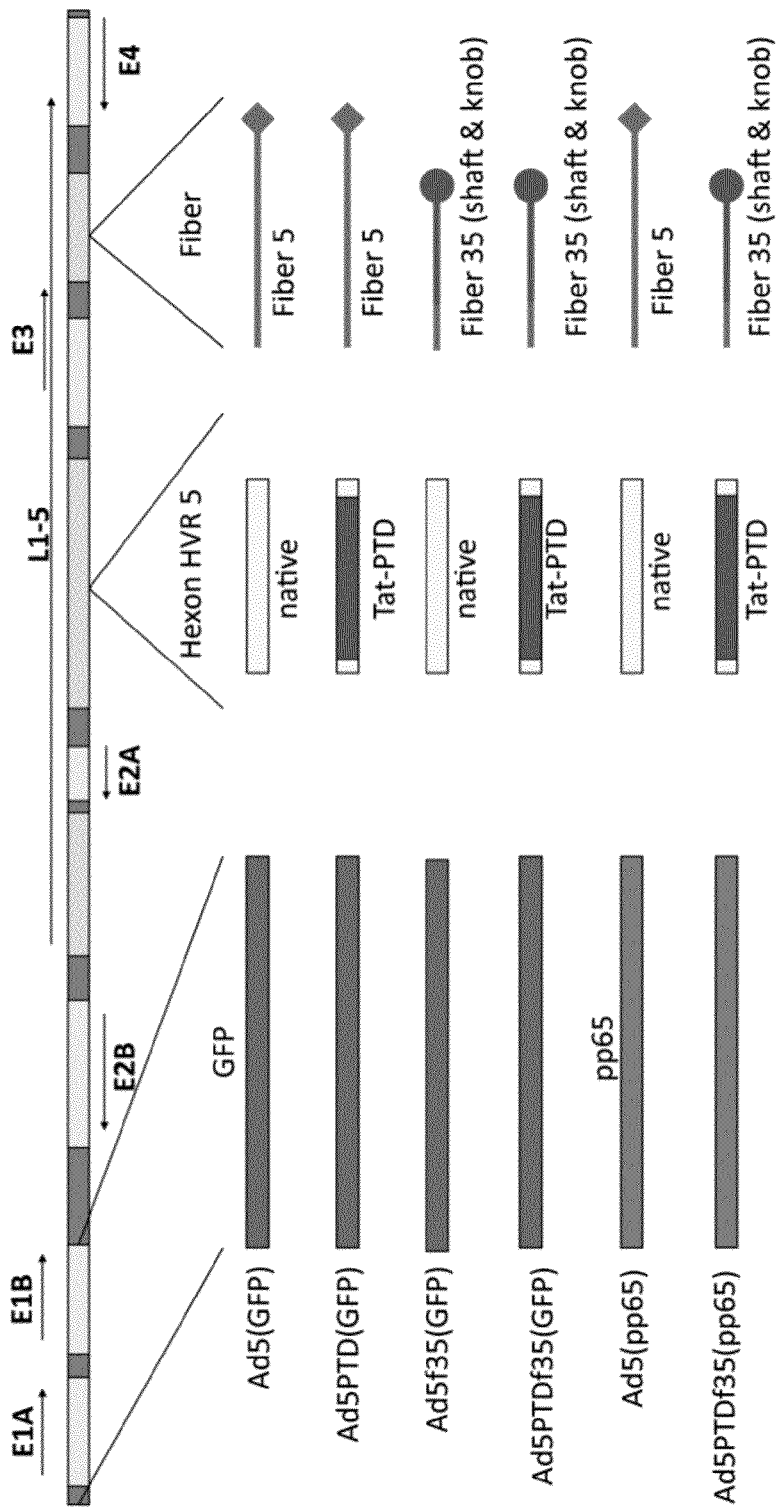

FIG. 8 is a schematic drawing of engineered viruses. All viruses are based on E1-delated human Ad5. The transgenes (GFP or pp65) are under control of the CMV immediate early promoter. The sequence encoding Tat-PTD was inserted into the hexon HVR5 region. The gene encoding the adenovirus fiber was either kept from Ad5 or replaced with the fiber from Ad35.

Figure 9:
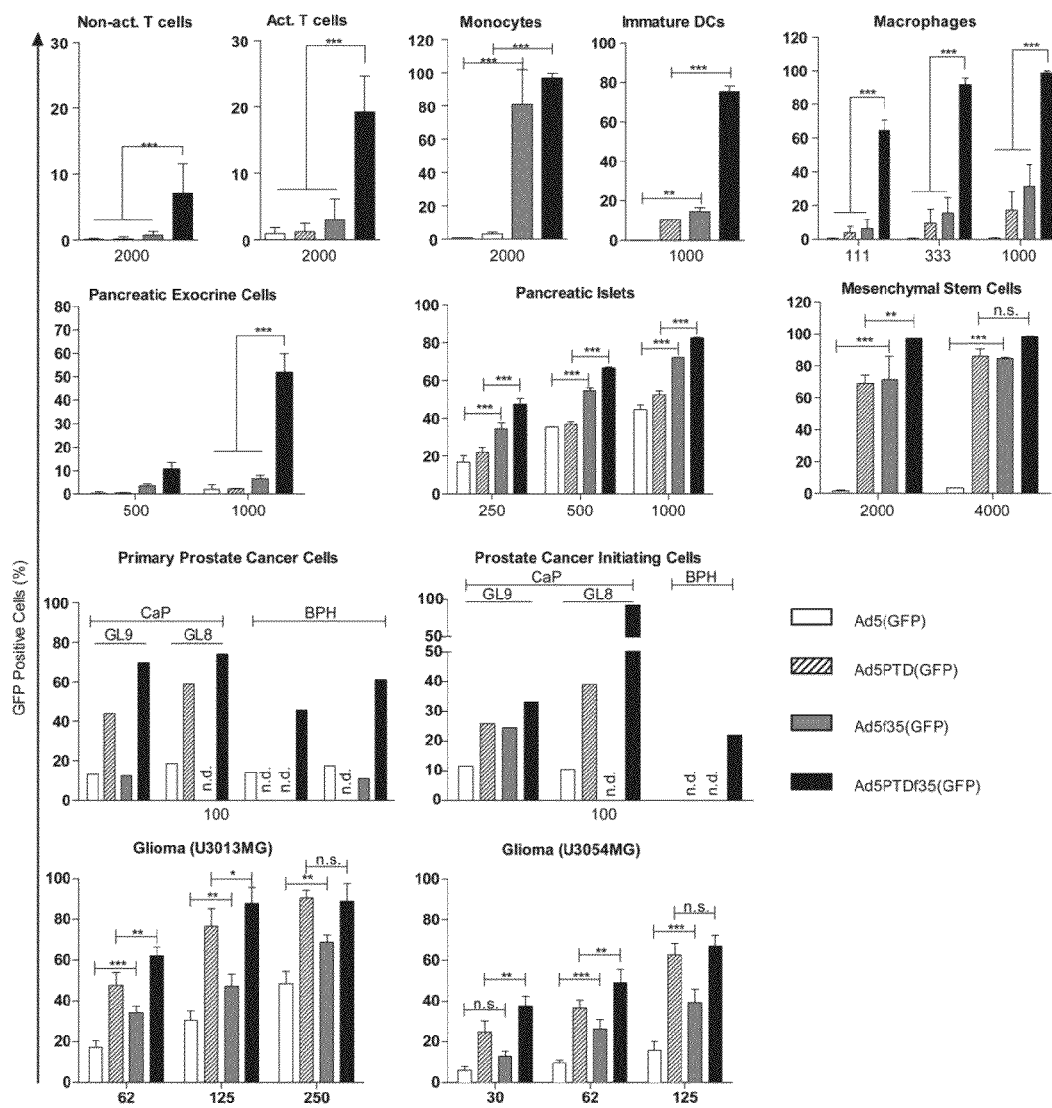

FIG. 9 shows the PTD-based adenovirus with fiber switched to f35 has dramatically increased gene delivery efficiency in primary cell cultures including: hematopoletic cells/subsets; pancreatic exocrine cells and islets; mesenchymal stem cells; primary prostate cancer cells and cancer initiating cells; primary glioma cells. Non-act. T cells: non-activated T cells. Act. T cells: activated T cells. DCs: dendritic cells. CaP: prostate cancer samples. GL: gleason grade. BPH: benign prostatic hyperplasia samples. n.d.: Not done. The numbers under x-axis indicate the evg/cell. Transduction level is presented as the percentage of GFP-positive cells. Experiments were repeated on cell cultures from 4-8 different donors (heamatopoietic cells, pancreatic exocrine cells, pancreatic islets) or the average of at least 3 independent experiments (glioma cells and mesenchymal stem cells). The data for prostate cancer samples were shown as each individual. Non-parametric student t-test was used for comparison between different groups. Error bar stands for standard deviation (SD). \*: p<0.05, \*\*: p<0.01, \*\*\*: p<0.001.

Figure 10:
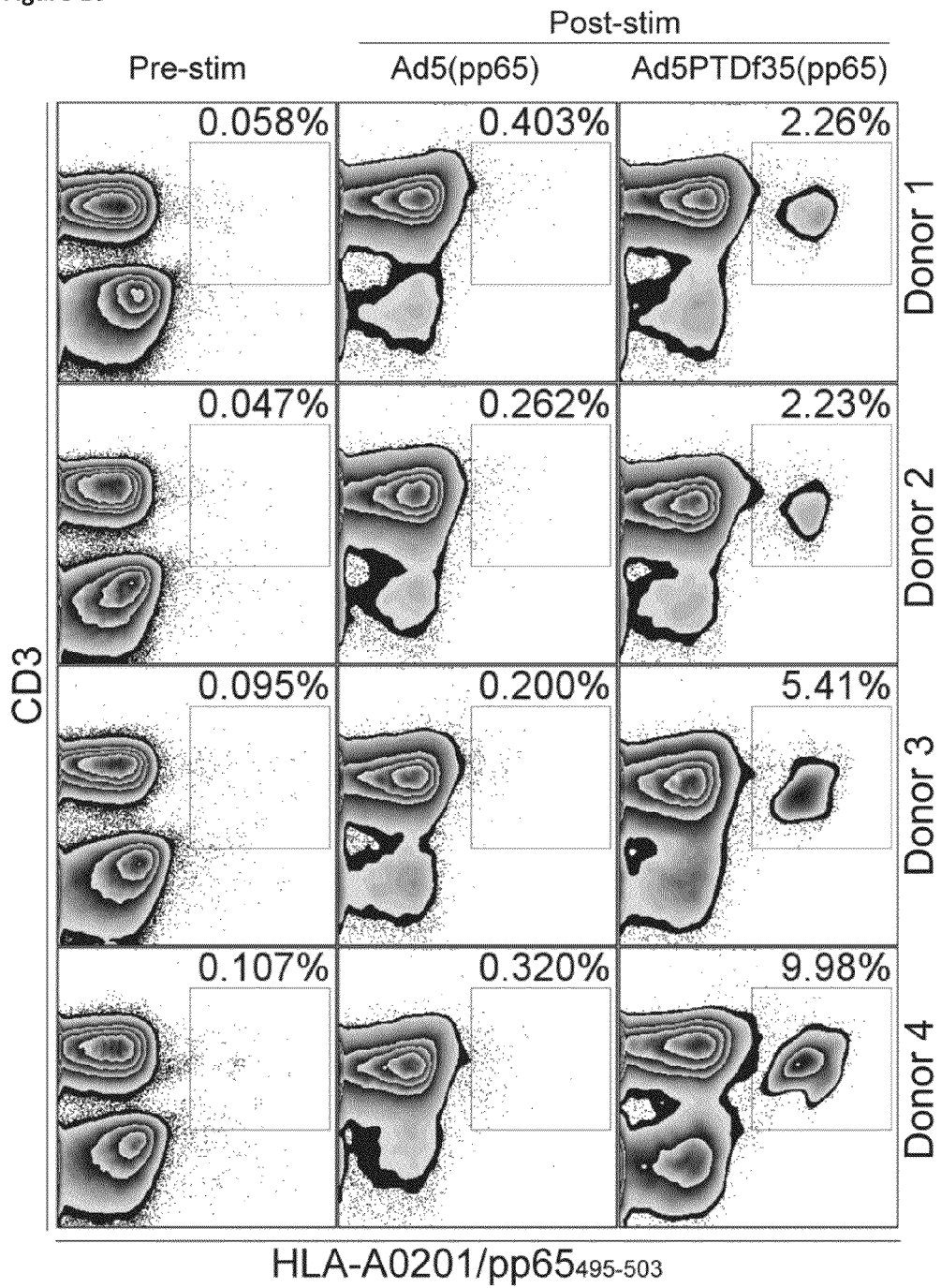

FIG. 10 shows the Ad5PTDf35-based adenovirus encoding the cytomegalovirus pp65 antigen (Ad5PTDf35(pp65)) can transduce DCs at a relatively low dosage with the purpose of expansion of antigen-specific T cells. T cells from four CMV-seropositive, HLA-A2-positive blood donors were co-cultured with Ad5(pp65) or Ad5PTDf35(pp65) transduced (100 evg/cell) autologous DCs for 11 days. DCs would process and present the pp65 peptide to T cell followed by specific T cell expansion. The frequency of CMV-pp65-specific T cells were evaluated by HLA-A\*0201/pp65$_{459-503}$ tetramer staining before (pre-stim) and 11 days after stimulation (post-stim). At a relative low virus load (100 evg/cell), Ad5PTDf35(pp65) has much higher efficiency in DCs modification than the native viral vector Ad5(pp65).

Figure 11:
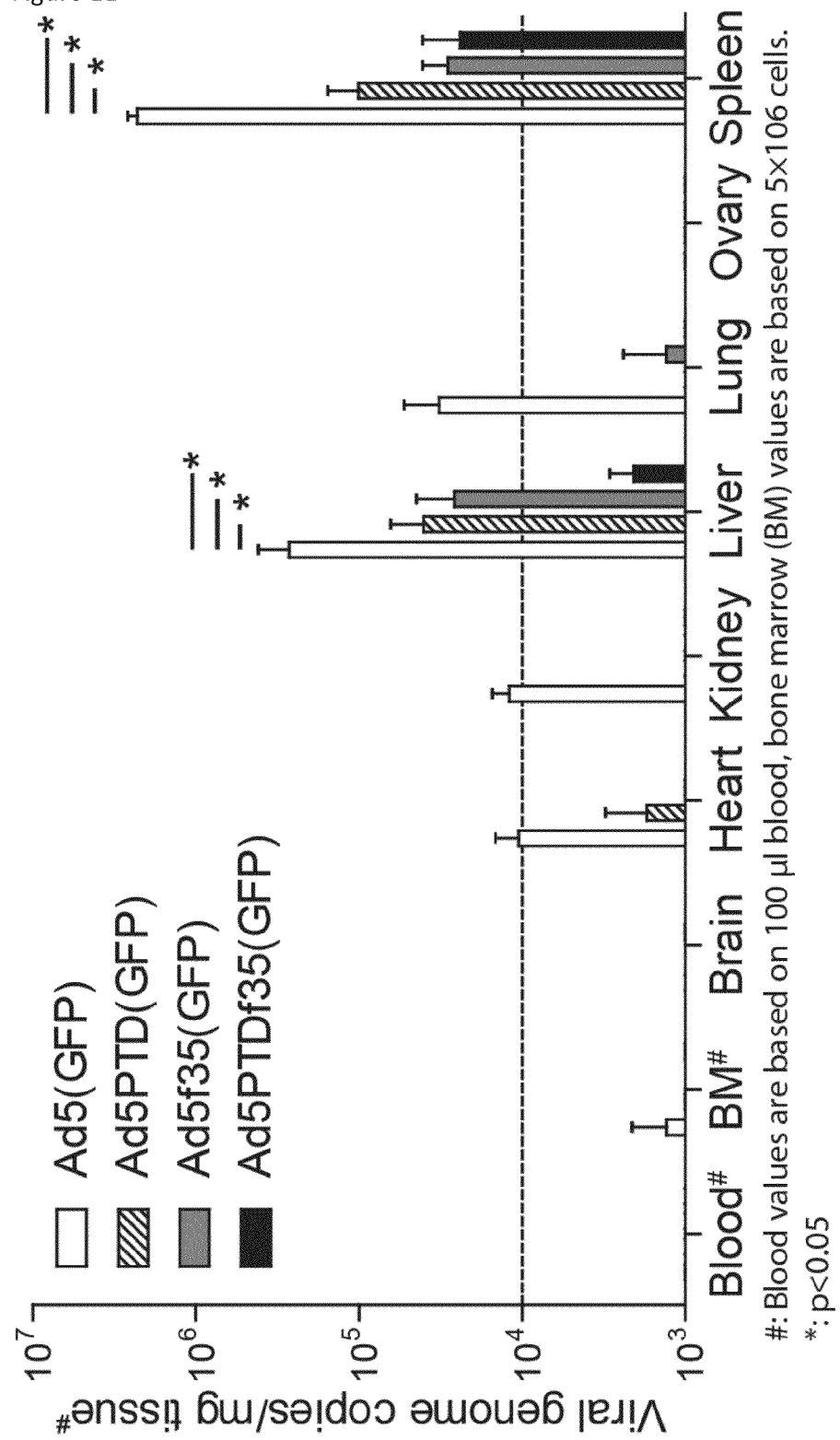

FIG. 11 shows biodistribution data in mice after intravenous (tail vein) injections of equal amounts of four different adenoviral vectors: Ad5(GFP), Ad5PTD(GFP), Ad5f35 (GFP) and Ad5PTDf35(GFP). The hexon modification of adenovirus dramatically reduced the viral liver toxicity.

Figure 12:
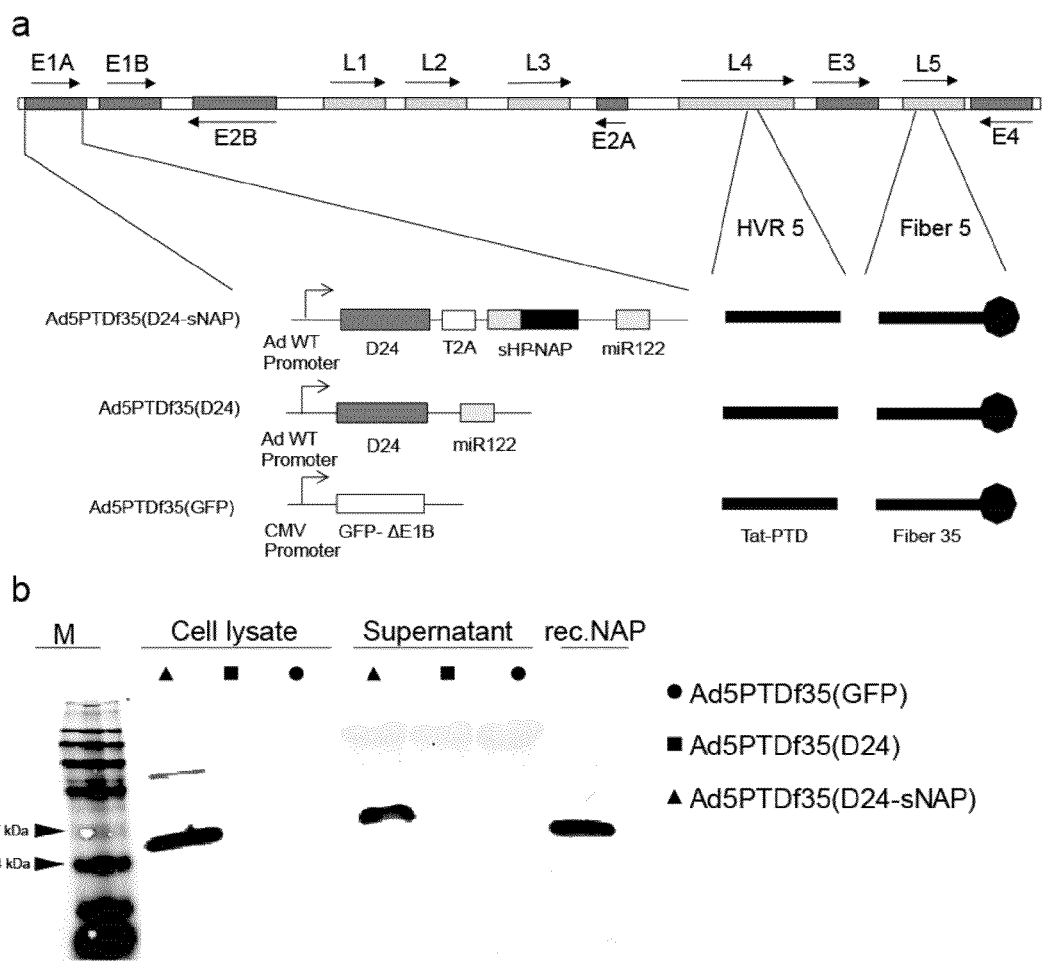

FIG. 12 is a schematic illustration of viruses used in the experiment and Western blot showing production of NAP. (a) Ad5PTDf35(D24-sNAP), Ad5PTDf35(D24) and Ad5PTDf35(GFP). (b) BON cells were transduced with Ad5PTDf35(D24-sNAP), Ad5PTDf35(D24) or Ad5PTDf35 (GFP) with or without blocking of protein secretion using Brefeldin A. Total cell lysate (where secretion was blocked with Brefeldin A) or supernatant were harvested 24 hours post-transduction and samples were resolved by 10% SDS-PAGE. HP-NAP was detected by Western blotting using anti-HP-NAP antibody (Clone 16F4). Recombinant HP-NAP protein was used as a positive control.

Figure 13:
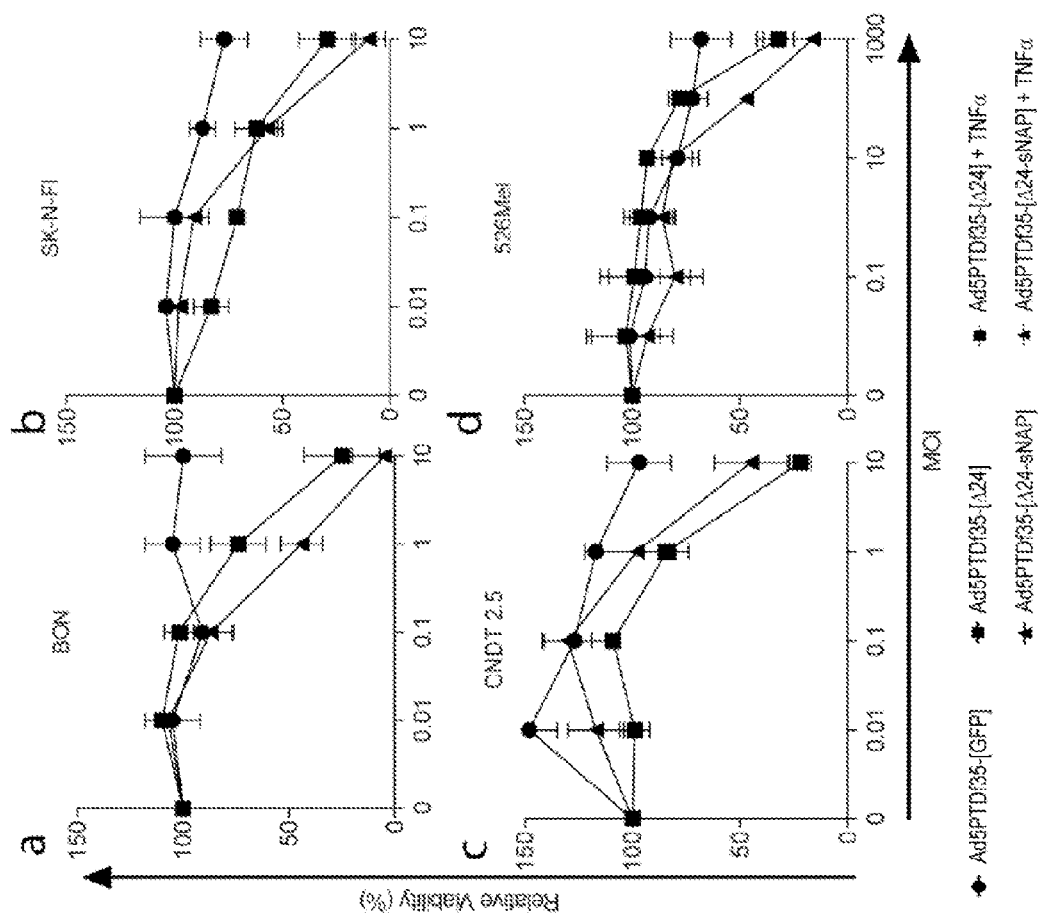

FIG. 13 shows the Ad5PTDf35-based oncolytic adenoviruses efficiently kill cancer cells from different origin in vitro. Cells of various origin (a, c) neuroendocrine tumor cell lines BON and CNDT2.5, (b) human neuroblastoma cell line SK-N-FI and (d) human melanoma cell line mel526 were transduced with Ad5PTDf35(D24-sNAP), Ad5PTDf35(D24) or Ad5PTDf35(GFP) at various MOI's ranging from 0.1-1000 FFU/cell in suspension for 2 hours and plated in a 96-well plate (10000 cells/well). Cell viability was examined 5 days post-transduction by MTS assay. Values represent viability in relation to untransduced cells. Mean+SD from triplicate samples are shown.

Figure 14:
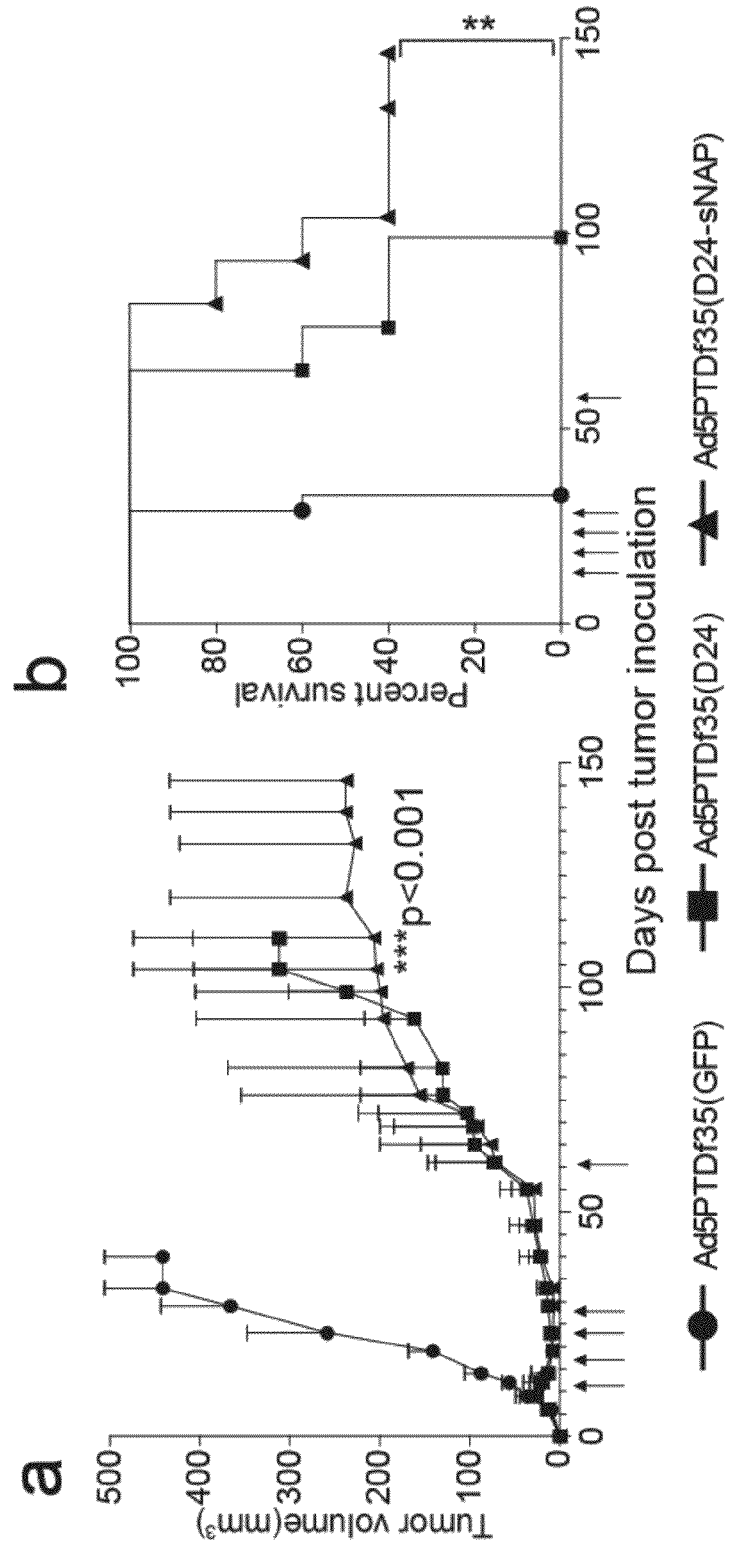

FIG. 14 show the Ad5PTDf35-based oncolytic adenoviruses efficiently delayed the tumor growth in vivo and significantly prolonged the median survival of tumor-bearing mice. BON ($5\times10^6$ cells) were injected s.c. in nude mice. The mice were treated with Ad5PTDf35(D24-sNAP), Ad5PTDf35(D24) or Ad5PTDf35(GFP) ($5\times10^8$ FFU/injection) at various time points indicated by arrows in the figures. Tumor growth was monitored by caliper measurements. (a) Tumor size curve for mice treated with different virus is shown. Values represent mean tumor volume ($mm^3$)+SEM (5 mice per group). Mice were sacrificed when tumor volume reached 800 $mm^3$ or if the tumors were ulcerated and wounded. Experiment was terminated 150 days post-tumor inoculation because no change in tumor volume was noticed during the final three weeks before termination of the experiment. Significant difference in tumor volume in Ad5PTDf35(D24-sNAP) treated mice was noted after day 99 (*$p<0.001$; n=5) (b) A Kaplan-Meier survival curve survival curve shows the survival data and log-rank test was performed for comparison. ($p<0.01$; n=5).

Figure 15:
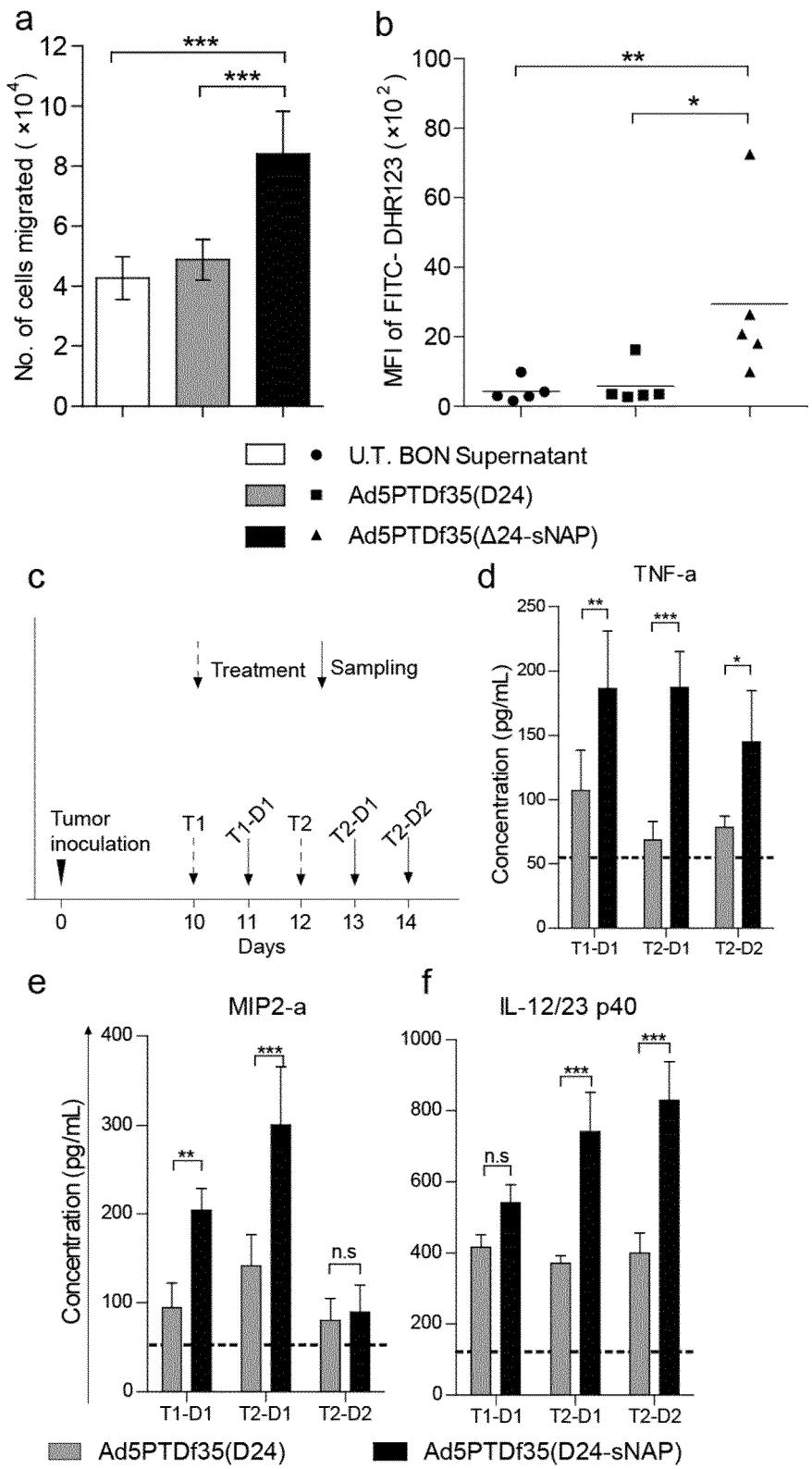

FIG. 15 shows the HP-NAP armed oncolytic adenovirus could recruit neutrophils both in vitro and in vivo and the secreted HP-NAP protein could induce proinflammatory and Th1 cytokine expression. BON cells were transduced with viruses Ad5PTDf35(D24-sNAP) or Ad5PTDf35(D24) at MOI 10 FFU/cell. Supernatants were harvested 48 hours post-transduction. (a) Transwell migration assay of human neutrophils isolated from 4 different individuals ($2\times10^5$ cells/well) against harvested supernatants for 2 hours at 37° C. All samples were analyzed in triplicates and the data is represented as mean±SD of number of cells migrated. Supernatant from untransduced BON cells were used as control, (*$p<0.001$; n=12). (b) Granulocyte activation assay with supernatants from virus-transduced BON cells for 30 minutes at 37° C. Activation was measured in terms of ROI production, which was monitored using fluorescent dye DHR123. Supernatant from untransduced BON cells were used as control. At least 10000 events were recorded in the flow cytometer and MFI of DHR123 was recorded, ($p<0.01$; *$p<0.05$; n=5). (c) Mice bearing BON tumors were treated with two intratumoral injections of Ad5PTDf35(D24-sNAP) or Ad5PTDf35($\Delta$24) (Indicated dotted arrows) and 2 mice per group were sacrificed, blood and tumor samples were drawn at different time points (indicated by solid arrows). Serum was separated from blood by centrifugation at 300 g for 10 min. Concentration of various cytokines determined by ELISA are represented in (d) TNF-$\alpha$, (e) MIP2-$\alpha$ and (f) IL12/23 p40. The dotted lines represent cytokine levels in the serum of untreated tumor bearing mice. All samples were analyzed in duplicates. Data represent mean concentration (pg/ml)+SD, (*$p<0.001$; $p<0.01$; *$p<0.05$; n=4).

Figure 16:
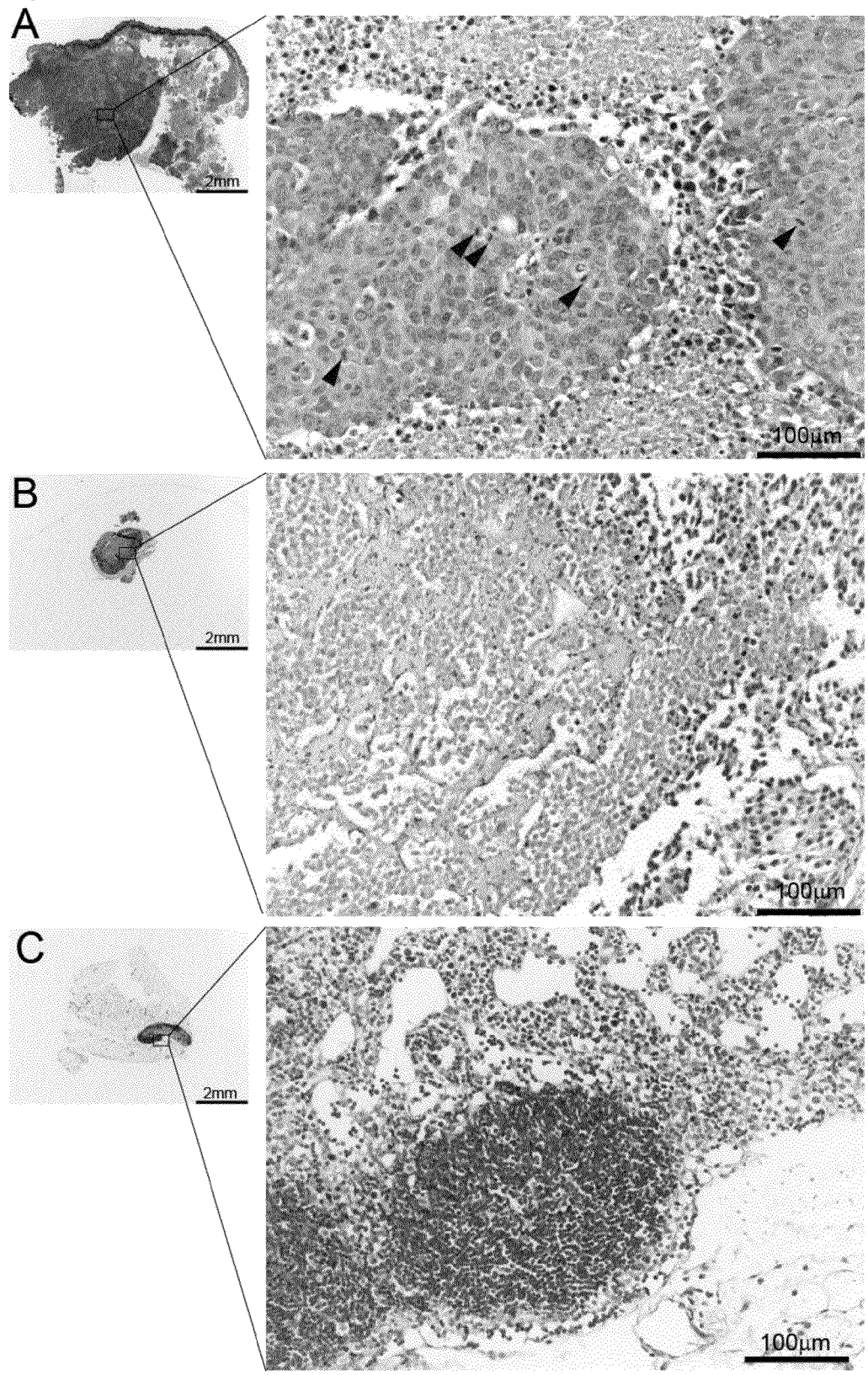

FIG. 16 represents histological H&E stained sections of the embedded tumor tissue, (a) isolated from an Ad5PTDf35(D24)-treated mouse on day 104 (mitotic cells are marked by arrows). (b, c) Representative pictures of histological H&E stained sections of the embedded tissues isolated from the two survivors of Ad5PTDf35(D24-sNAP)-treated mice when the non-growing tumors were resected on day 146. Original magnification, left panel ×12.5, right panel ×200; scale bar: left panel 2 mm, right panel 100 µm.

Figure 17:
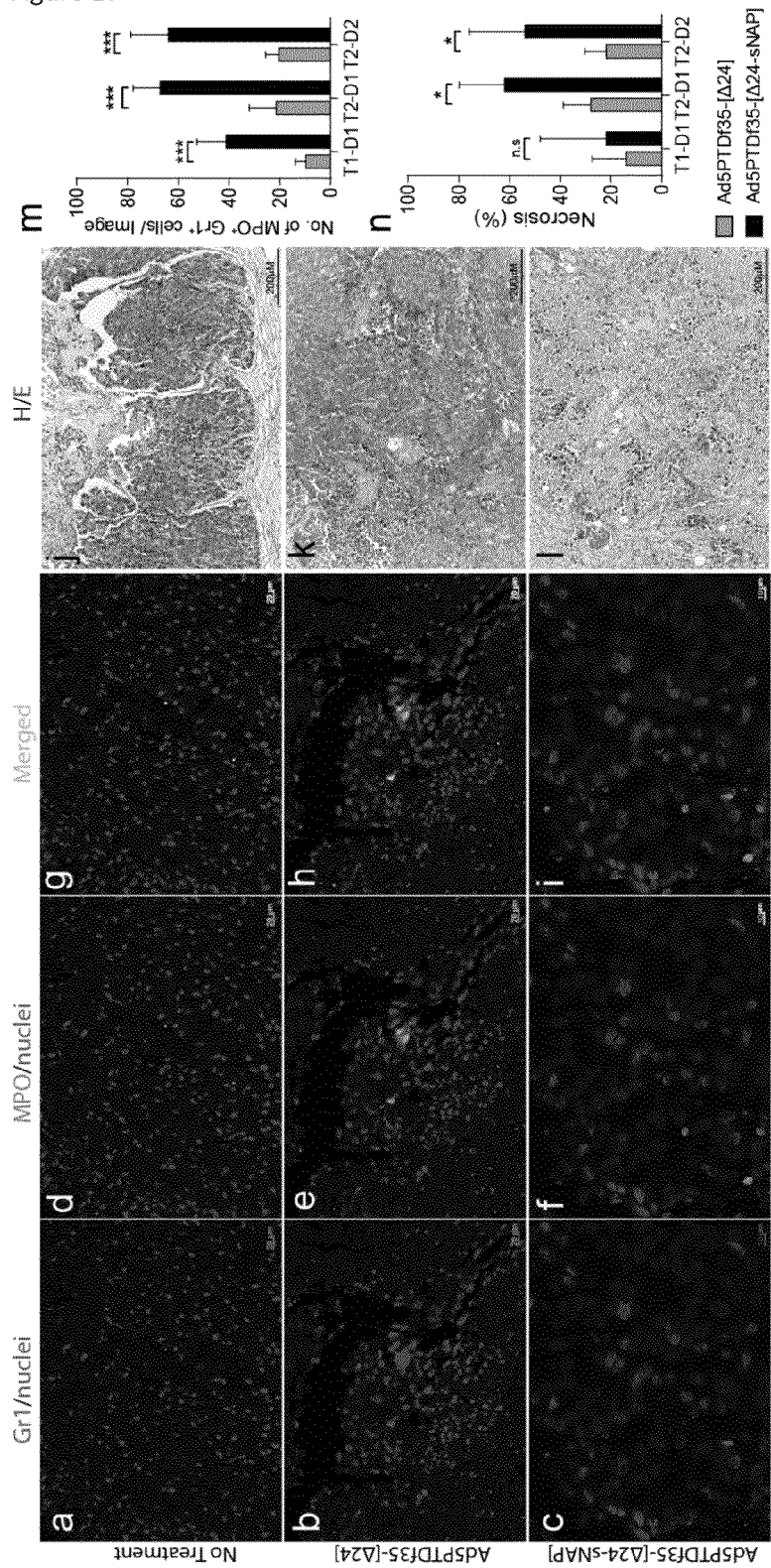

FIG. 17 shows the neutrophil infiltration and necrotic areas in tumor sections harvested from mice after therapy with HP-NAP-armed adenovirus. Mice bearing BON tumors were treated with two intratumoral injections of Ad5PTDf35(D24-sNAP) or Ad5PTDf35(D$\Delta$24) and 2 mice per group were sacrificed, tumor samples were drawn at different time points as Illustrated in FIG. 15c. Immunofluorescence staining of paraffin embedded tumor tissue sections after the following (a, d, g) no treatment (original magnification ×200; scale bar: 20 µm), (b, e, h) treatment with Ad5PTDf35(D24) (original magnification ×200; scale bar: 20 µm) and (c, f, i) treatment with Ad5PTDf35(D24-sNAP) on T2-D1 (original magnification ×400; scale bar 10 µm). The staining was performed with the myeloid differentiation marker Alexa-647-$\alpha$-Gr1, the neutrophil-specific enzyme Alexa-488-$\alpha$-MPO and nuclear stain Hoechst 33342. Representative pictures of histological H&E stained sections of the embedded tumor tissue after (J) no treatment, (k) treatment with Ad5PTDf35(D24) and (l) treatment with Ad5PTDf35(D24-sNAP) on T2-D1 (original magnification ×100; scale bar: 200 µm). (m) The number of Gr1+/MPO+ cells in tumor/image at 200× original magnification after treatment with virus at different time points. The data represent mean±SD (***$p<0.001$; n=5). (n) Quantitative analysis of necrosis in the tumor sections after treatment with viruses at different time points. The data represent mean±SD (n.s.: no significance; *$p<0.05$; n=5).

Figure 18:
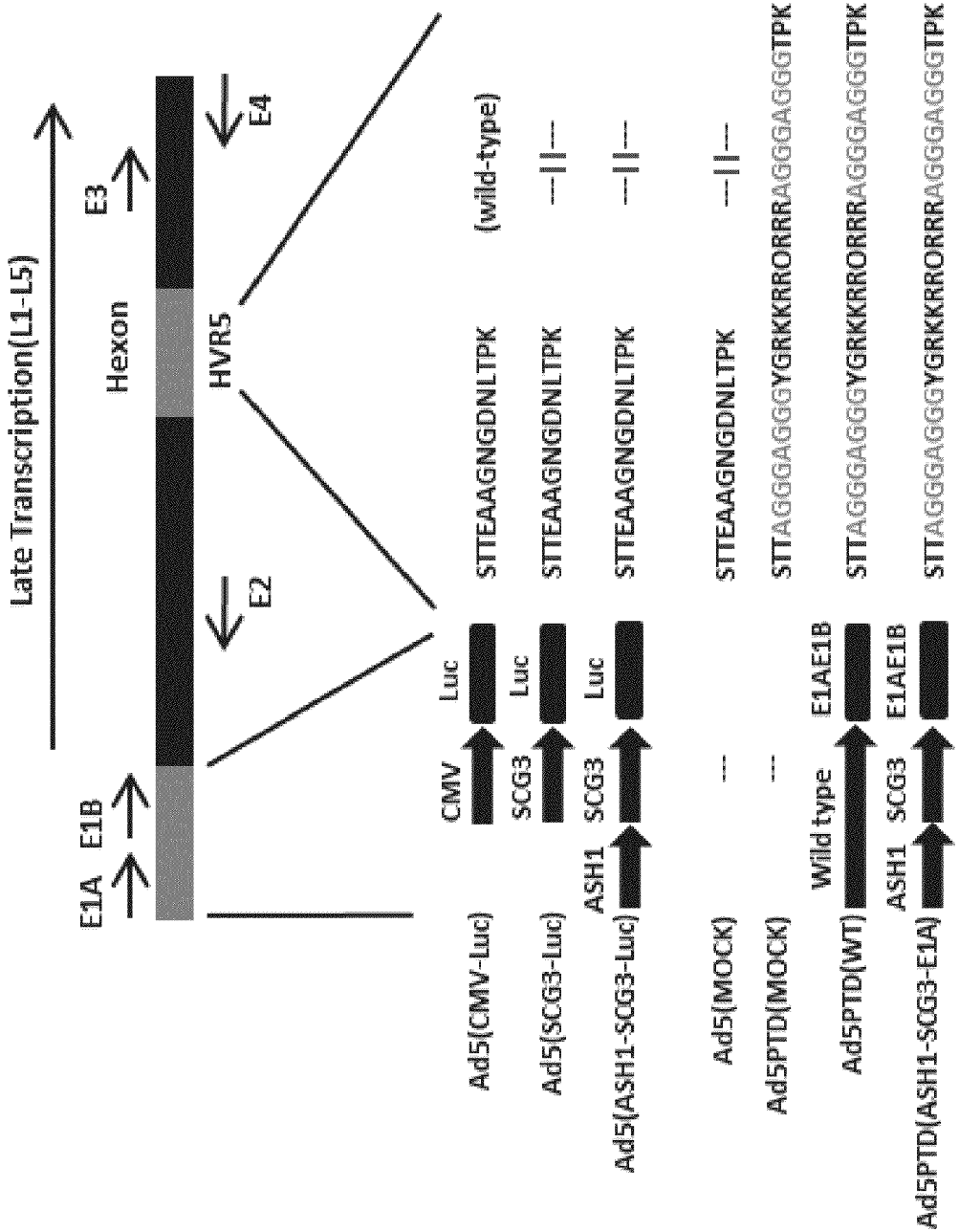

FIG. 18 is a schematic illustration of vectors and viruses used. Ad5(MOCK) and Ad5PTD(MOCK) are E1-deleted replication-defective control viruses. The oncolytic viruses Ad5PTD(WT) and AD5PTD(ASH1-SCG3-E1A) as well as Ad5PTD(MOCK) have Tat-PTD modification in hexon HVR5 region. Ad5PTD(ASH1-SCG3-E1A) are Ad5PTD-based adenovirus that the E1A gene is under control of SCG3 promoter and 0.2 kb human ASH1 enhancer.

Figure 19:
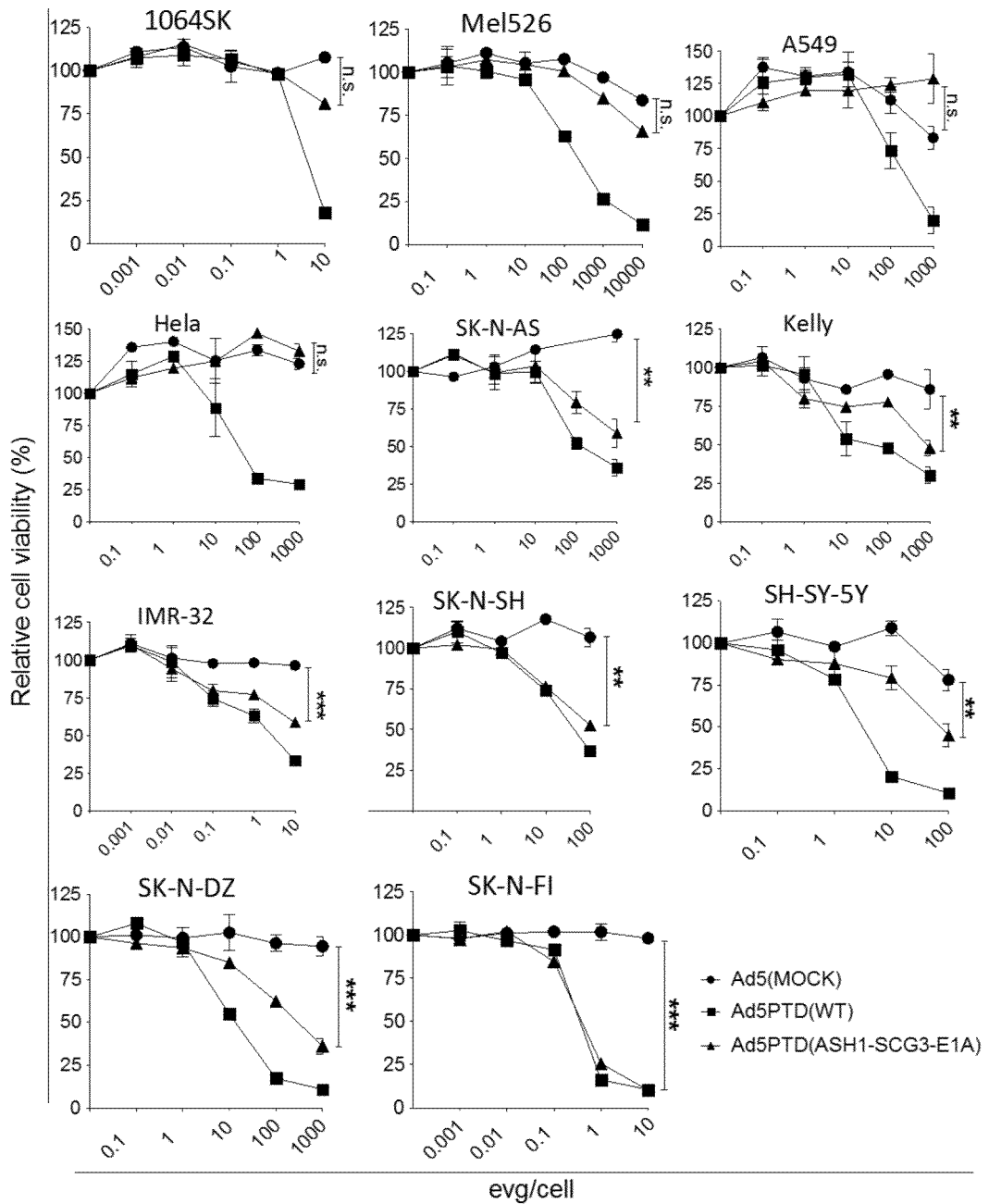

FIG. 19 shows that Ad5PTD(ASH1-SCG3-E1A) possesses selective killing of neuroblastoma cells. Neuroblastoma cell lines (SH-SY-5Y, IMR-32, SK-N-DZ, SK-N-AS, Kelly, SK-N-FI, SK-N-SH), non-neuroblastoma tumor cell lines (MeI526, A549, Hela) and normal fibroblast cells (1064SK) were transduced with Ad5PTD(ASH1-SCG3-E1), Ad5PTD(WT) or Ad5(MOCK) virus. The relative cell viability was analyzed 4 days after virus transduction by MTS assay. All data are shown as mean±SD from three independent experiments each with triplicate samples (, $p<0.01$, *, $p<0.001$).

Figure 20:
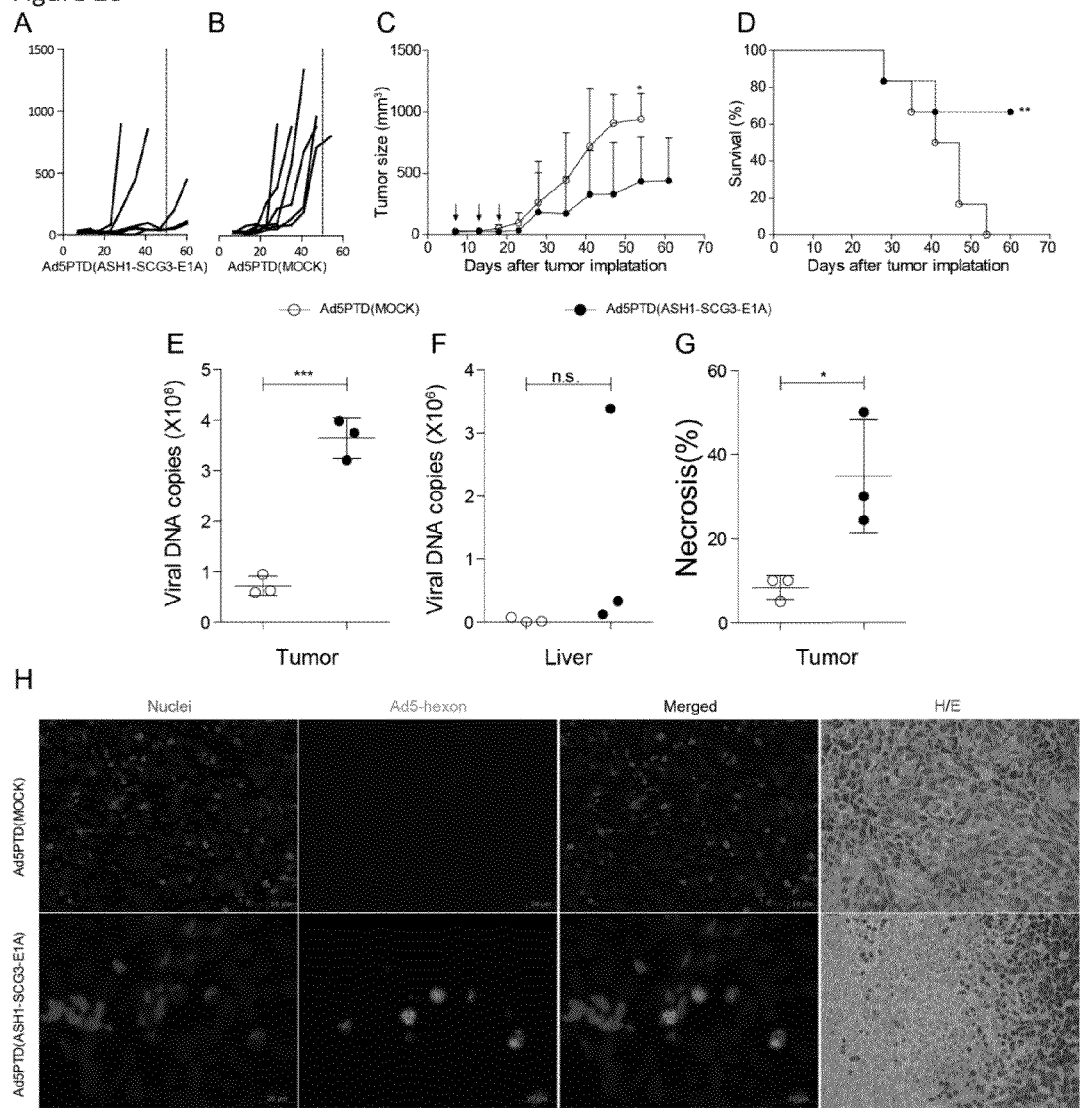

FIG. 20 shows that treatment with Ad5PTD(ASH1-SCG3-E1A) delays tumor growth and prolongs survival in nude mice with transplanted human neuroblastoma tumor. NMRI-nude mice bearing subcutaneous human neuroblastoma, SK-N-FI, tumors were treated by peritumoral virus injection at day 7, 13, 18 after tumor implantation. The tumors were monitored by caliper measurements. Six mice per group were used. Mice were sacrificed when the tumor size reached 900 $mm^3$. The experiment was terminated at day 60 after tumor implantation. (A) Tumor sizes of individual mice treated with Ad5PTD(ASH1-SCG3-E1A). (B) Tumor sizes of individual mice treated with the control virus Ad5PTD(MOCK). (C) Tumors sizes for the two groups of treated mice shown as mean±SD (*: $p<0.5$). (D) A Kaplan-Meier survival curve shows survival data. Log-rank test was used to compare survival curves. (**: $p<0.01$). Three mice from each group were sacrificed on day 21. The tumor (E) and liver (F) were analyzed by qPCR to detect virus DNA. Percentage of tumor necrosis caused by virus treatment was evaluated in a blinded manner by an experienced pathologist (G). Tumor sections were also immuno-fluorescently stained to detect progeny of replicated viral particles (H).

Figure 21:
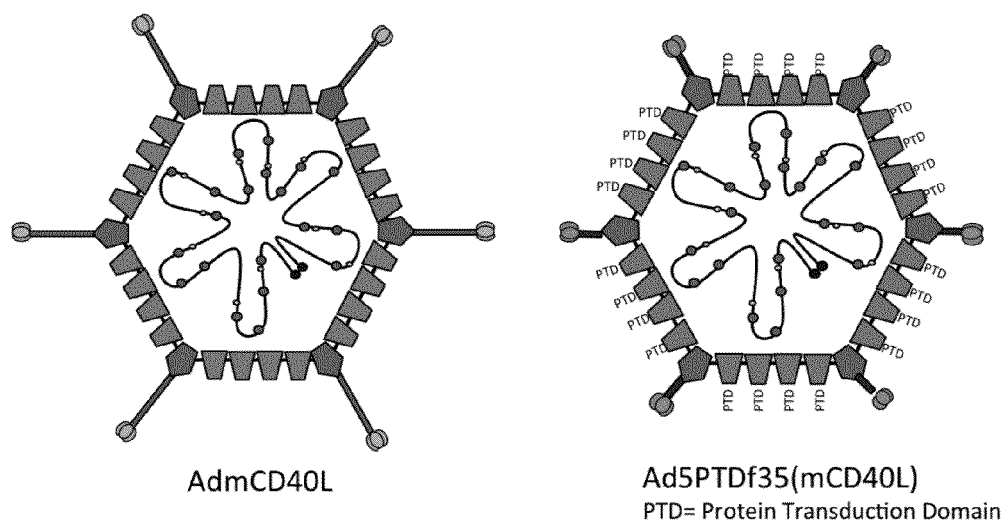

FIG. 21 is a schematic illustration of a non-replicative Ad5-based adenoviral vector expressing the murine CD40L transgene (left) and a non-replicative Ad5PTDf35-based adenoviral vector expressing the murine CD40L transgene (right).

Figure 22:
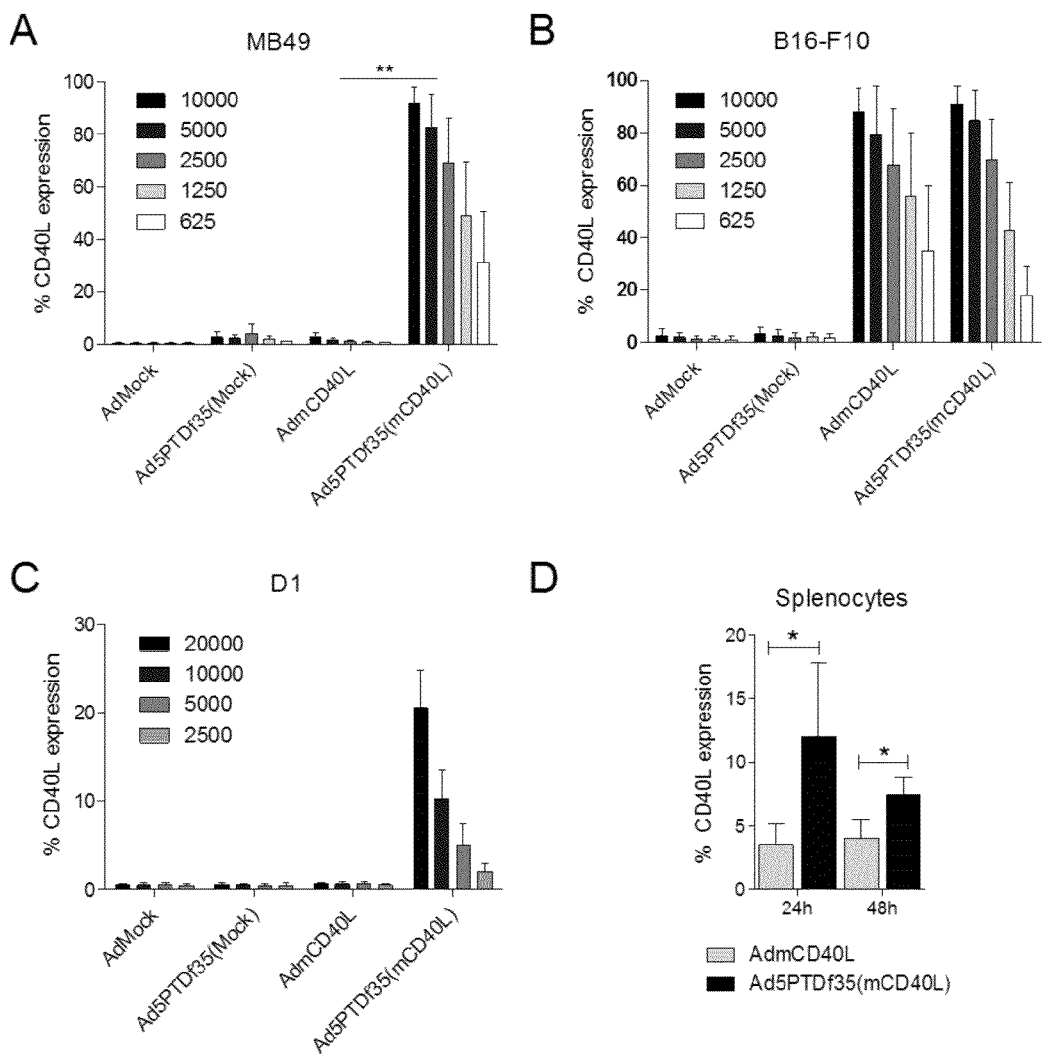

FIG. 22 shows the comparison of AdmCD40L versus the Ad5PTDf35(mCD40L). Mock viruses (AdMock and Ad5PTDf35(Mock)) were used as controls. AdmCD40L means Ad5(mCD40L) and AdMock means Ad5(Mock). CD40L expression was determined 48 hours after transduction in (A) mouse bladder cancer cells (MB49), (B) mouse melanoma cell (B16-F10) and (C) mouse dendritic cells (D1) at different concentrations (evg/cell). (D) Splenocytes, activated with αCD3, αCD28 and IL-2, were transduced with 20000 evg/cell of either AdmCD40L or Ad5PTDf35 (mCD40L) and CD40L expression was evaluated at 24 hours after transduction by flow cytometry using an anti-CD40L antibody. The figures demonstrate results from three independent experiments. * $p<0.05$, ** $p<0.01$ with the Mann-Whitney test.

Figure 23:
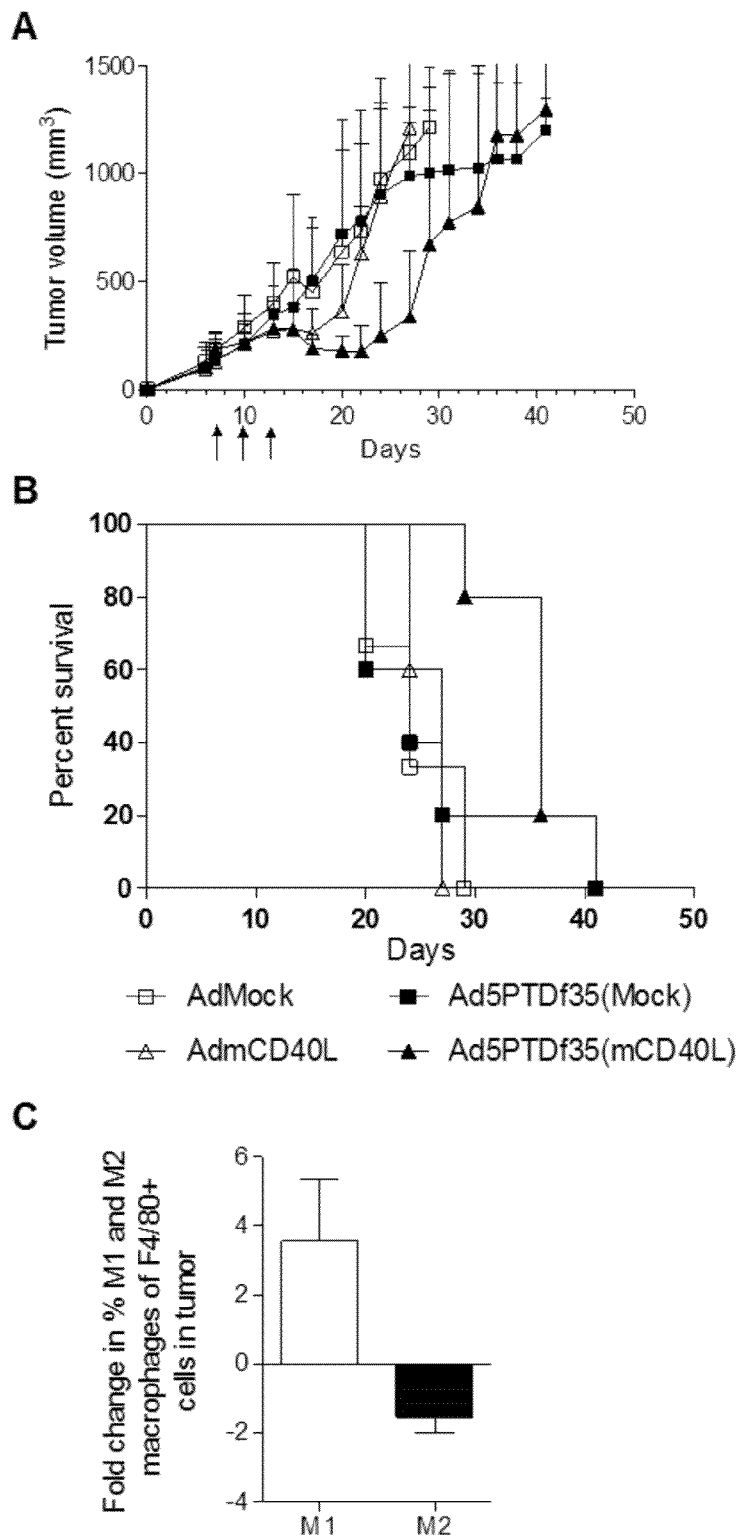

FIG. 23 shows comparison of therapeutic effect of AdmCD40L and Ad5PTDf35(mCD40L) vectors on established s.c MB49 tumors on female C57/BL6 mice (day 0). Three treatments were given intra-tumorally with three days apart at the concentration of $5\times10^9$ evg. (A) Tumor growth was measured and followed on all animals in the treatment groups AdMock (n=3), Ad5PTDf35(Mock) (n=5), AdmCD40L (n=5) and Ad5PTDf35(mCD40L) (n=5). Arrows demonstrate days of treatment. (B) Survival curve of the animals in (A). (C) Tumors from animals (n=4 in each group) were stained to look for the different types of macrophage population 24 hours after the last treatment. The percentage of M1 macrophages and M2 macrophage in the Ad5PTDf35(mCD40L)-treated tumors where compared to that in the AdmCD40L-treated tumors. It shows an increase for M1 macrophages and decrease of M2 macrophages for Ad5PTDf35(mCD40L)-treated tumors compared to AdmCD40L-treated tumors, wherein the $F4/80^+CD11b^+CD11c^+CD206$ cells are defined as M1 macrophages, while the $F4/80^+CD11b^+CD11c^+CD206^+$ cells are defined as M2 macrophages.

Figure 24:
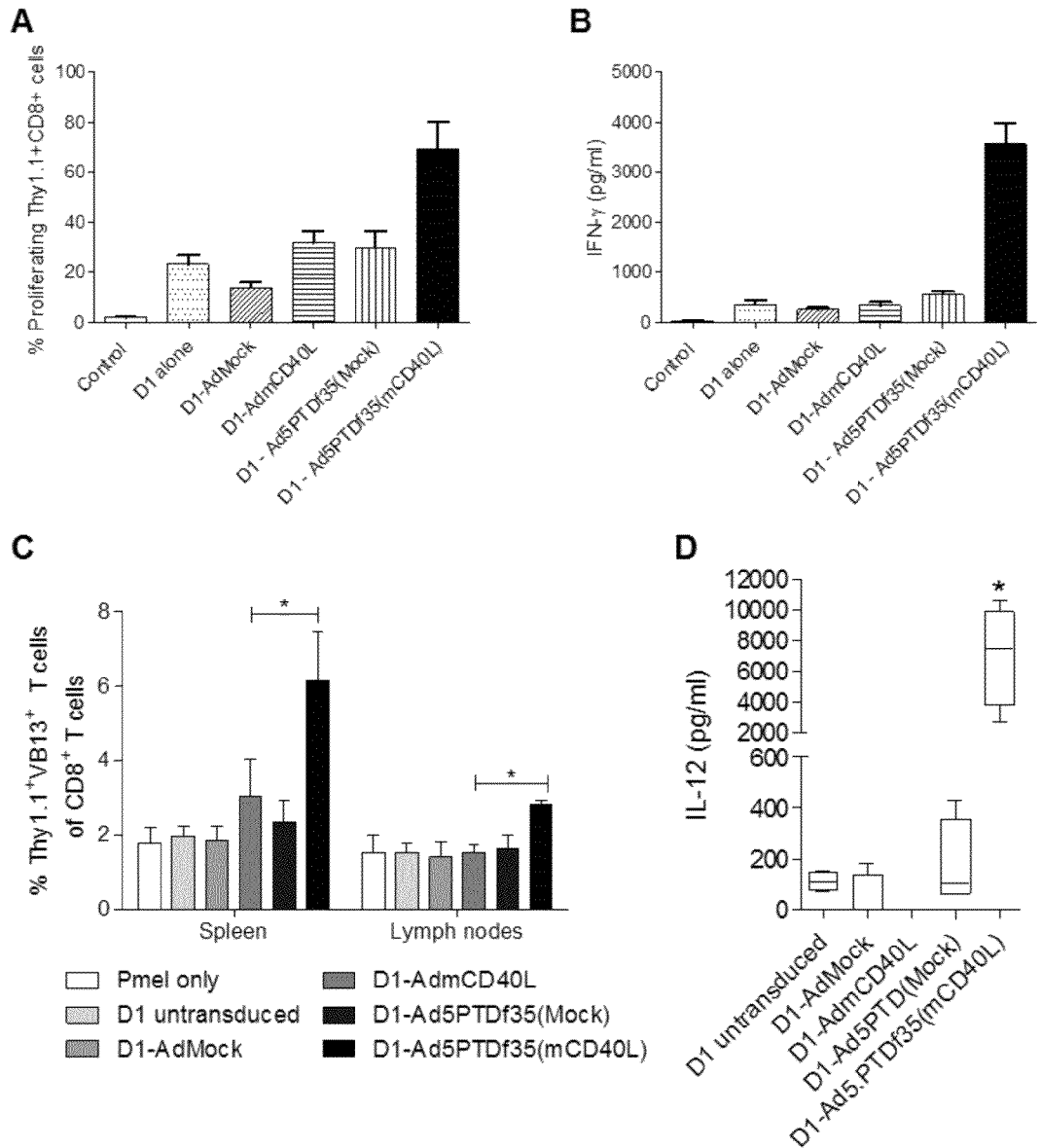

FIG. 24 shows that Ad5PTDf35(mCD40L) improves the antigen presentation by the mouse dendritic cells D1 and that this leads to improved T cell quality for T cells interacting with the adenovirus vector-transduced D1 cells. (A) The percentage of proliferating T cells with hgp100-specific TCR ($Thy1.1^+$ and $CD8^+$) after interaction with adenovirus vector-transduced (AdMock, AdmCD40L, Ad5PTDf35(Mock), Ad5PTDf35(mCD40L)) or untransduced, hgp100 peptide-loaded, D1 cells. The peptide was added at a concentration of 0.025 ng/ml. (B) Supernatant from the co-cultures was collected and analyzed for IFN-γ. (C) Antigen presentation assay in vivo. Splenocytes from PmeI mice (having hgp100-specific TCR in their $CD8^+$ T cell population) were intravenously injected into immunocompetent C57/BL6 mice and 24 hours later virus-transduced, hgp100-loaded D1 cells were injected intravenously. Four days later the animals were sacrificed, spleen and lymph nodes were collected and analyzed for the percentage of hgp100-specific T cells in the CD8 T cell population. The improved antigen presentation can be explained by improved CD40L augmentation as well as the increased IL-12 secretion by D1 cells (FIG. 24D). * $p<0.05$ with the Mann-Whitney test.

Figure 25:
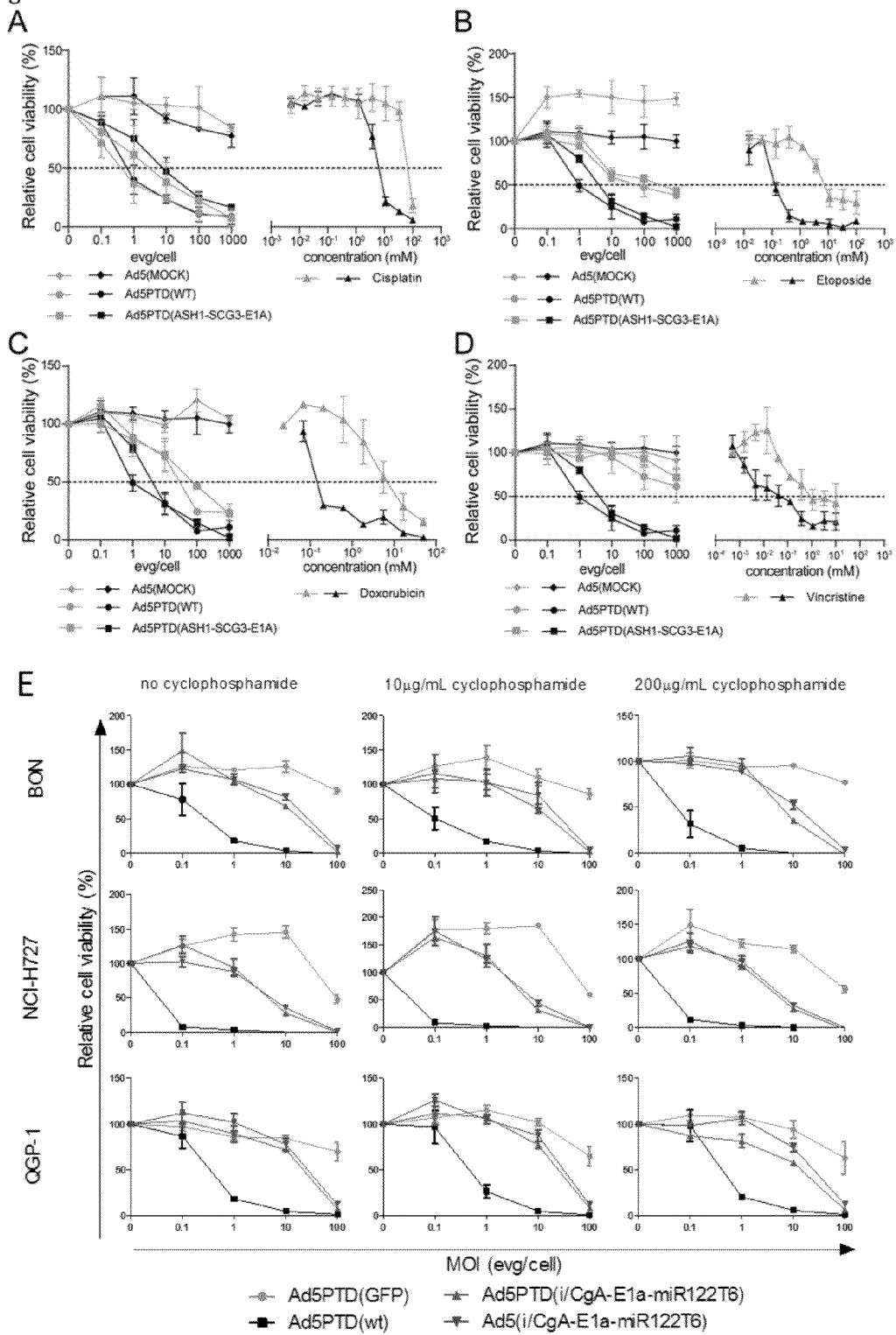

FIG. 25. Oncolytic adenovirus in combination with chemotherapy drugs. A cisplatin-insensitive clone of SK-N-FI and doxoru bicin-insensitive, etoposide-insensitive and vincristine-insensitive clones of SH-SY-5Y were established through repeated cycles of culture with increasing drug concentration. (A-D) Drug-sensitive (black lines) and drug-insensitive (grey dotted lines) neuroblastoma cells were then treated with viruses or drugs. The relative cell viability was analyzed after 4 days by MTS assay. (A) Oncolytic virus and cisplatin killing of SK-N-FI cells. (B) Oncolytic virus and etoposide killing of SH-SY-5Y cells. (C) Oncolytic virus and doxorubicin killing of SH-SY-5Y cells. (D) Oncolytic virus and vincristine killing of SH-SY-5Y cells. All data are shown as mean±SD from four independent experiments each with triplicate samples. (E) BON, NCI-H727 and QGP-1 cell lines were treated with PTD-based oncolytic adenovirus Ad5PTD (i/CgA-E1a-miR122T6) with different evg/cell in absence or presence of 10 μg/mL or 200 μg/mL cyclophosphamide. The relative cell viability was analyzed after 6 days by MTS assay.

DETAILED DESCRIPTION

The invention generally refers to the hexon Tat-PTD modified adenoviruses and uses thereof.

Unless defined otherwise, all technical and scientific terms used herein have the meaning commonly understood by a person skilled in the art to which the present invention belongs. The following references provide a general definition of many of the terms used in this invention: Dictionary of microbiology and molecular biology (Singleton et al., 3rd ed, Revised, 2007, ISBN: 9780470035450); The Cambridge dictionary of science and technology (Walker, 1990, ISBN: 9780521394413); Glossary of Genetics: Classical and Molecular (Rieger et al., 5th ed., 1991, ISBN: 9783540520542); HarperCollins dictionary of biology (Hale, 1991, ISBN: 9780064610155); Gene IX (Lewin, 2007, ISBN: 9780763740634); Field's Virology (Knipe et al., 5th ed., 2007, ISBN: 9780781760607). For clarity of the invention, the following definitions are used herein.

The term "nucleotide sequence" or "DNA/RNA sequence" refers to polymer composed of nucleotide units (ribonucleotides, deoxyribonucleotides, related naturally occurring structural variants, and/or synthetic non-naturally occurring analogs thereof) linked via phosphodiester bonds, related naturally occurring structural variants, and/or synthetic non-naturally occurring analogs thereof. A sequence is usually presented from its 5 prime end to 3 prime end.

The term "coding sequence" or "coding nucleotide sequence" refers to a polynucleotide with the properties of being able to be transcribed into either a defined sequence of nucleotides (tRNA, rRNA and mRNA) and, in the case of mRNA transcription, being further translated into a polypeptide. The coding sequence may be a gene, a cDNA or a recombinant nucleic acid.

The term "Tat-PTD" refers to a nucleotide sequence that is derived from the HIV-1 Tat protein (amino acid 47-57) with 2 short linker flanking on both side. The amino acid sequence is 5'-AGGGAGGGYGRKKRRQRRRGGGAGGGA-3', (SEQ ID NO: 2) wherein 5'-AGGGAGGG-3' and 5'-GGGAGGGA-3' are the short linker sequences.

"Promoter" is the minimal nucleotide sequence required to direct transcription. The promoter may include elements that render the promoter-depending gene expression cell-type or tissue specifically controllable or inducible by external signals or agents.

"Enhancer" refers to a regulatory sequence that increases expression of an operatively linked gene or coding sequence but does not have promoter activity. An enhancer can generally be provided upstream, downstream and to the other side of a promoter without significant loss of activity. Furthermore, an enhancer may be positioned within the coding sequence of the gene.

The term "transgene" refers to a polynucleotide sequence with the properties of being able to be transcribed into either a defined sequence of nucleic acids (tRNA, rRNA and mRNA) and, in the case of mRNA transcription, being further translated into a polypeptide. The coding sequence may be a gene, a cDNA or a recombinant nucleic acid. It also refers to any nucleic acid sequence that is inserted by artifice into a cell and becomes part of the genome of the cell and preferably of an organism developing from that cell. The sequence may either be stably integrated or provided as a stable extrachromosomal element.

The term "gene expression cassette" is a nucleotide sequence consists of a promoter, gene sequence (including both the coding sequence and/or the non-coding sequence) and a transcriptional stop signal. The gene expression cassette can sometimes be only the gene coding sequence if there is other promoter and transcriptional stop signal presented. The person skilled in the art knows reference to a gene expression cassette.

The term "therapeutic gene(s)" is a nucleotide sequence that codes for a "therapeutic molecule" in form of a defined sequence of nucleic acids (i.e., RNA) or a defined sequence of amino acids which, when expressed, can be used to treat or ameliorate a disorder, by treating the cause of the disorder or by lessening the detrimental effect of, the symptoms of the disorder. Thus a therapeutic gene may code for a therapeutic molecule in form of a short interfering RNA, antisense RNA, ribozyme or polypeptide.

The term "Adenoviral vector" or "adenovirus based gene delivery vector" refers to an adenovirus that has been genetically modified to have a gene expression cassette inside the adenoviral genome. The gene expression cassette can be inserted either in the E1 gene region of the adenoviral genome or anywhere else. This kind of vector is used to deliver the inserted gene product to cells and/or tissues via adenovirus transduction. This kind of vector can be replication-defective or replication-competent depending on whether the E1A gene (or other replication-essential genes) of the adenovirus was deleted or not.

The term "oncolytic adenovirus" or "oncolytic adenoviral agent" or "oncolytic vaccine" refers to an adenovirus that has been genetically modified (or naturally selected) to have a specific/selective replication in and lysis the targeted tumor cells.

The term "Ad5" refers to adenovirus serotype 5. "Ad5-based" refers to any products developed based on Ad5.

The term "Ad5f35" refers to adenovirus serotype 5 with the fiber from serotype 35.

"Ad5f35-based" refers to any products developed based on Ad5f35.

The term "Ad5PTD" refers to an Ad5 adenovirus with Tat-PTD sequence inserted in the hexon. "Ad5-based" refers to any products developed based on Ad5PTD.

The term "Ad5PTDf35" refers to an Ad5PTD adenovirus with fiber from human adenovirus serotype 35. "Ad5PTDf35-based" refers to any products developed based on Ad5PTDf35.

The word "a" or "an" shall not be construed as excluding the plural, i.e. reference to e.g. the use of "a molecule" does not exclude the use of plural molecules.

Description of the Hexon Tat-PTD Modified Adenovirus

Adenoviruses are widely used for gene transduction and oncolytic therapy. This invention provides a genetic modified adenovirus with increased viral transduction efficiency and means to overcome the fiber-masking problem.

Briefly, the present invention involves hexon Tat-PTD genetic modification of adenoviruses. The Tat-PTD sequence was genetically introduced in hyper variable region 5 (HVR5) of the hexon protein, the major coat protein of the virus capsid, to add a CAR independent route of adenovirus infection. Most studies report modifications of either the HI-loop or the C-terminus of the adenovirus fiber. Some reports also show modification on minor capsid protein such as pIIIa, pIX. The inventors decided to modify the hexon HVR5 site since there are 240 hexon trimers expressed on the adenoviral surface versus only 12 fiber trimer molecules and that hexon modification would not affect the native fiber binding and thereby native route of infection. Moreover, the hexon modification would keep the targeting agent away from the fiber. The Ad5PTD-based viruses could transduce CAR-negative tumor cells and dramatically increase the degree of transduction of CAR-positive tumor cells. The efficacy of Tat-PTD-modified oncolytic Ad5 viruses was increased in vitro, which resulted in an improved therapeutic effect in vivo. The Ad5PTD-based oncolytic virus was not blocked by soluble Ad5 fibers to the same extent as non-modified Ad5 and yielded larger plaques than non-modified Ad5, indicating that the Ad5PTD-based viruses are able to overcome the fiber-masking problem.

Description of Using Tat-PTD Modified Adenoviruses as Gene Delivery Vectors

The invention also involves the uses of hexon Tat-PTD modified adenoviruses as gene delivery vectors. Adenoviruses could be developed as gene delivery vectors to deliver foreign genes into cells/tissues. Ad5PTD-based viral vector enhanced the gene delivery efficiency in both CAR-negative cells and CAR-positive cells. By using green fluorescent protein (GFP) as reporter gene, Ad5PTD-based vector could transduce the CAR-negative cell line SK-N-SH up to 90%, whereas the unmodified adenovirus completely failed to transduce SK-N-SH. The Ad5PTD-based vector also increased the transduction of CAR-positive cell line such as HuVec and A549. The mechanism of cellular uptake and cell penetration of CPPs has been studied for decades and still remains divergent. Different models have been proposed to describe the mechanism. In general, these models can be categorized as energy-dependent endocytosis and direct translocation via the lipid bilayer [7]. In our case, the exact transduction mechanism of the Tat-PTD modified viruses is unclear. We are able to transduce CAR-negative cells with the Tat-PTD-modified viruses and the transduction can only be partly blocked by soluble fiber molecules, which strongly indicates that a CAR-independent pathway is utilized for cellular uptake.

In clinical use with the intention of cancer therapy, adenoviral vectors can be modified to express a therapeutic gene that directly kill tumor cells or to express a immune modulatory gene that trigger the immune system to attack tumor cells or to express a regulatory gene that alter the vasculization of tumors or alter the microenvironment within tumors. One example of a therapeutic gene would be thymidine kinase from herpes simplex virus (HSV-TK) or yeast or bacterial cytosine deaminase. Expression of HSV-TK in tumor cells leads those tumor cells susceptible to the cytotoxic effects of ganciclovir. Other examples of therapeutic genes are proapoptotic genes such as BAX, BID, BAK or BAD that would induce apoptosis of tumor cells. Examples of modulatory genes that attract the immune system to attach tumor cells are CD40 ligand (CD40L or CD154) and granulocyte macrophage colony-stimulating factor (GM-CSF) or histidine-rich glycoprotein (HRG). Local expression of CD40L in tumor area leads to activation of dendritic cells, which leads to further activation/expansion of tumor-reactive T cells. This can in many cases lead to regression or elimination of tumors.

HRG inhibits tumor growth and metastasis by inducing macrophage polarization (skewing tumor-associated macrophage away from the M2- to a tumor-inhibiting M1-phenotype) and vessel normalization through down-regulation of platelet growth factor. Since the Tat-PTD modified adenovirus has a broadened tropism, it is more efficient to express transgenes like CD40L and HRG in the tumor area and the viral dosage could be dramatically scaled down.

Description of Using Tat-PTD Modified Adenoviruses as Oncolytic Agents

The invention also involves the uses of hexon Tat-PTD modified adenoviruses as oncolytic agents. Adenoviruses could be developed as oncolytic agents, which mean cancer cell killing agents. Recombinant oncolytic adenovirus is usually genetically engineered to restrict the viral replication in cancer cells. The therapeutic effects are an outcome of viral replication in and lyse the cancer cells. Restricted viral replication is achieved by using a tumor-specific or tissue-specific promoter to control the replication essential viral gene E1a expression and/or a mutated version of E1a gene that leads to a selected replication in cancer cells. Ad5PTD-based oncolytic viruses enhanced the oncolysis of CAR-negative cells and retain the same oncolysis efficacy of CAR-positive cells. Intratumoral injection of Ad5PTD-based oncolytic adenovirus inhibits subcutaneous tumor xenograft of CAR-negative cells in both NMRI-nude and SCID/beige mice models. The treatment of Ad5PTD-based oncolytic adenovirus prolonged the survival of tumor bearing mice compared with treatment of un-modified virus or placebo (Phosphate saline buffer).

In clinical use with the intention of cancer therapy, Ad5PTD-based oncolytic adenoviruses can be further controlled by a tumor-specific or tissue-specific promoter driving expression of viral genes essential for virus replication or mutations or deletions of the E1a gene making it selective for tumor cells. As an example, Ad(I/PPT-E1A) [8, 9] possess selective replication in prostate cells thanks to the recombinant I/PPT promoter and Ad(CgA-E1A) [10] and Ad(CgA-E1A-mir122) [2] possess selective replication in neuroendocrine cells thanks to the human chromogranin A (CgA) promoter. Likewise, Ad5PTD(ASH1-SCG3-E1A) possesses selective replication in neuroblastoma cells thanks to the human achaete-scute complex homolog 1 (ASH1) enhancer and human secretogranin 3 (SCG3) promoter. Viruses where the E1a gene is controlled by for example the human telomerase reverse transcriptase (hTERT), cyclooxygenase 2 (Cox2), survivin and/or E2F-1 promoters show selective replication in tumor cells over normal cell. Other examples are Ad5PTD(D24) and Ad5PTDf35, which possess selective replication in tumor cells with deficiency in the retinoblastoma protein (pRb) pathway. The deleted adenoviral E1A protein expressed upon infection cannot bind to the pRB in normal cells and therefore not bring the host cell into S-phase of the cell cycled and thus not replicate in normal cells. Ad5PTD-based oncolytic adenoviruses can be directly injected into the tumor area and thanks to virus replication in infected tumor cells, the tumor cells would be lysed/killed. Since the PTD-based viruses have an increased oncolytic efficacy, the therapeutic outcome would be improved and/or the dosage could be reduced to lower the side effects. The virus could be injected intratumorally, peritumorally and/or be given intravenously or intraperitoneally. Intravenous administration may have the benefit to treat tumor metastases and circulating tumor cells as well and/or prevent formation of tumor metastases.

The invention also involves means to overcome the fiber-masking problem by using hexon PTD-modified oncolytic adenoviruses. The adenovirus fiber protein is expressed in huge excess during the cycle of viral infection-replication [5]. It was reported that the excess fiber proteins, which are released from infected cells before mature viral particles lyse the cells, masks the receptors on uninfected cells in the vicinity thereby, preventing the second round of progeny virus infection [5]. This property hampers the spread of oncolytic virus within tumors. By using GFP reporter gene assays, we found that the transduction of Ad5PTD-based vector retained 80% transduction efficacy in the presence of soluble fiber while soluble fiber molecules blocked the transduction of unmodified viral vector. Furthermore, the plaques formed by Ad5PTD-based oncolytic virus were on average 1.6 times larger than the plaques formed by unmodified Ad5-based oncolytic virus. In contrast to chemically conjugated Tat-PTD-modified virus [11] or HI-loop/C-terminus Tat-PTD-modified virus [12], which would only enhance the first round of infection, the present invention provides a hexon modified virus, which utilizes a CAR-independent cellular transduction pathway, and enhances all rounds of infection and can therefore overcome the fiber-masking problem. The plaque formation assay confirmed that Ad5PTD(wt) spreads faster than Ad5(wt) in a 2-dimensional model, which implicates that the Tat-PTD-modified virus should spread faster also in 3-dimensional structural tumors in vivo.

Tat-PTD modified virus could be further modified by replacing the fiber molecule to that from another serotype for viral re-targeting. Ad5PTDf35(D24) is an example that the fiber was switched from serotype 5 to serotype 35 and the viral targeting molecule thereby switched from CAR to CD46. It possesses tumor cell-specific replication thanks to a 24 bp deletion in the E1A gene. Ad5PTDf35-based viruses exhibit better cancer cell killing efficacy and gene delivery. Moreover, oncolytic virus could also be armed with therapeutic genes to enhance the therapeutic outcome. Ad5PTDf35 (D24-sNAP) is an example of oncolytic virus that is armed with the neutrophil activating protein from *Helicobacter pylori* (HP-NAP). HP-NAP is a chemo-attractant that can recruit neutrophils to the site of infection and it is also a potent immunomodulator, capable of inducing secretion of proinflammatory cytokines and promotes T helper 1 (Th1) type immune polarization. Combining viral oncolysis and immune response against tumors, Ad5PTDf35(D24-sNAP), which secretes a soluble form of HP-NAP, was found to give the best therapeutic outcome in the laboratory animal model. Therapeutic genes for adenovirus arming are not restricted to HP-NAP. As mentioned above, the therapeutic gene can be another immunomodulator such as CD40L, GM-CSF or HRG, a proapoptotic gene such as BAX, BID, BAK or BAD, a cytotoxic gene such as diphtheria toxin or pseudomonas exotoxin or a suicide gene such as HSV-TK or cytosine deaminase.

Oncolytic virus based on Ad5PTDf35 can also be generated by controlling the adenovirus E1a genes expression using a tumor-specific or tissue-specific promoter and/or microRNA target sequences. We have previously described that the PPT promoter [8] can selectively drive viral replication in normal and neoplastic prostate cells [8, 9], the CgA promoter can selectively drive viral replication in normal and neoplastic neuroendocrine cells [13], the secretogranin (SCG)-3, SCG2, NESP55 promoters and ASH1 enhancer can selectively drive viral replication in neuroblastoma cells. The off-target cytotoxicity can be further reduced by using microRNA de-targeting through the introduction of microRNA target sequences in the virus genome. We have reported this example by using miR122 target sequence, to reduce liver toxicity [2]. We strongly believe that a combination of tissue specific promoter and Ad5PTD-based or Ad5PTDf35-based virus could improve virus transduction and tissue specificity for cancer treatment.

The adenovirus according to the invention may be included in a pharmaceutical composition for delivery to a subject in need thereof. Such compositions may additionally include a stabilizer, enhancer or other pharmaceutically acceptable carriers or vehicles. A pharmaceutically acceptable carrier can contain a physiologically acceptable compound that acts, for example, to stabilize the adenovirus, optionally comprising a therapeutic gene. A physiologically acceptable compound can include, for example, carbohydrates, such as glucose, sucrose or dextrans, antioxidants, such as ascorbic acid or glutathione, chelating agents, low molecular weight proteins or other stabilizers or excipients. Other physiologically acceptable compounds include wetting agents, emulsifying agents, dispersing agents or preservatives, which are particularly useful for preventing the growth or action of microorganisms. Various preservatives are well known and include, for example, phenol and ascorbic acid. One skilled in the art would know that the choice of pharmaceutically acceptable carrier, depends on the route of administration and the particular physio-chemical characteristics of the adenovirus. Examples of buffers, carriers, stabilizers or adjuvants can be found in Remington: The Science and Practice of Pharmacy $22^{nd}$ ed (Allen, L.V. (ed.) Pharmaceutical Press, London, 2012), incorporated herein by reference.

In clinical practice, the PTD-based adenovirus can also be administrated to patients in combination with one or more chemotherapeutic drugs, including drugs that have direct effects on cell division/function or DNA synthesis, drug that have an indirect effects on tumor cells and tumor microenvironment or drugs effecting the host immune system and thereby providing growth advantage for the adenovirus. Examples of drugs with a direct effect on tumors include alkylating agents, antimetabolites, plant alkaloids, kinase inhibitors, etc. Examples of drugs affecting the tumor microenvironment are hormones, metalloproteinases and anti-angiogenic agents, etc. Examples of drugs affecting the immune system includes antiproliferative immune suppressants such as mycophenolate mofetil, azathioprine, sirolimus etc.; Calcineurine Inhibitors such as cyclosporine, tacrolimus etc.; Corticosteroids such as prednisone, methylprednisolone etc.; Anti-lymphocyte antibodies such as rituximab, alemtuzumab, Ipilimumab etc.; Other antibodies such as tocilizuma, natalizumab, basiliximab, golimumab etc.; Other immune suppressing agents such as cyclophosphamide, interferons, CP-690,550, mTOR inhibitors etc. Adenovirus can also be used in combination with radiotherapy or other treatments like surgery or traditional Chinese medicine (herbal medicine, acupuncture, etc.).

Not only humans but also animals can be treated with the PTD-based adenovirus.

EXAMPLES

Example 1

The Generation of Hexon Tat-PTD Modified Adenovirus, so Called Ad5PTD-Based Vectors/Viruses All recombinant adenovirus were generated based on λ-phage mediated-recombineering in *E. coli* strain SW102 using bacmid pAdZ5-CV5-E3+ [14]. This bacmid contains the adenovirus serotype 5 genome, with the E1 region replaced by a selection/counter-selection cassette (als cassette) consisting of the bla (ampicillin resistance), lacZ (beta galactosidase) and sacB (sucrose resistance) genes. To generate pAd5(GFP), the CMV-GFP cassette was PCR amplified from Ad5(GFP) [15] using primers pF.Shuni and pR.Shuni and purified by gel extraction. Heat activated and freshly made competent *E. coli* SW102 cells containing pAdZ5-CV5-E3+ were electroporated with 100 ng PCR product using Gene Pulser II (Bio-Rad Laboratories, Hercules, Calif.). Selection was performed on LB-sucrose plates, containing LB without NaCl, 6% sucrose, 200 μM of isopropylthio-β-D-1-galactoside (IPTG, Sigma-Aldrich, St. Louis, Mo.) and 40 μg/ml of 5-bromo-4-chloro-3-indolyl-βD-galactopyranoside (X-Gal, Invitrogen). Positive colonies were designated pAd5(GFP).

To generate a scar-free modification in hexon HVR5, the selection/counter-selection method was used. Briefly, the als cassette was PCR amplified using primers pF.HVR5-als and pR.HVR5-als and knocked in into the HVR5 site in pAd5 (GFP). Selection was performed on LB agar plates containing 100 μg/ml of Ampicillin, 200 μM of IPTG and 40 μg/ml of X-Gal. Positive colonies were designated pAd5(GFP, HVR5als). Next, the als cassette was replaced by the Tat-PTD motif to generate pAd5PTD(GFP). Selection was performed on LB-sucrose plates. The Tat-PTD motif fragment was generated by joint-PCR with primer pairs pF1.HVR5-PTD/pR1.HVR5-PTD and pF2.HVR5-PTD/pR2.HVR5-PTD.

pAd5PTD(wt) and pAd5PTD(D24) were generated in the same manner by replacing the CMV-GFP cassette from the E1 region with serotype 5 wildtype E1A-E1B or E1A(D24)-E1B sequences. The als cassette was amplified using primers pF.E1-als/pR.E1-als to replace the CMV-GFP cassette. pF.Shuni and pR.Shuni were used for amplification of either the E1 region from wild type adenovirus DNA or E1-D24 region from plasmid AdEasy(D24).fk3. The PCR products were then used for replacement of the als cassette in the E1 region to generate pAd5PTD(wt) and pAd5PTD(D24) respectively. The viruses generated from pAd5PTD(GFP), pAd5PTD(wt) and pAd5PTD(D24) were named Ad5PTD (GFP), Ad5PTD(wt) and Ad5PTD(D24). All primers used can be found in FIG. 7.

Example 2

The Uses of Ad5PTD-Based Adenovirus as Gene Delivery Vectors

Adenoviral vectors are widely used as gene transfer vehicles. They efficiently introduce foreign genes into cells expressing CAR, the native receptor for Ad5 infection. Here the inventors compared the gene transduction capacity of two GFP-expressing adenoviral vectors in a range of cell lines. Ad5(GFP) use the same infection route as wild-type Ad5 while Ad5PTD(GFP) in addition to the Ad5 infection route has the Tat-PTD sequence in HVR5 of the hexon protein on the virus capsid and can infect cells via these cell-penetration (Tat-PTD) sequence. SK-N-SH, MB49, CNDT2.5 and 1064SK are CAR-negative or have low CAR expression levels, whereas A549, mel526, HuVec, BON express moderate to high levels of CAR (FIG. 3). Ad5PTD(GFP) showed efficient transduction of CAR-negative cell lines while Ad5 (GFP) showed no or very poor transduction of these cells (FIG. 3). Furthermore, transduction of CAR-positive cell lines by Ad5PTD(GFP) was always more efficient or as efficient as transduction with the unmodified Ad5(GFP) (FIG. 3).

These results indicate that insertion of a small cell penetrating peptide, herein Tat-PTD sequence, into the adenoviral hexon protein surface HVR5 region dramatically enhances adenovirus transduction ability.

The delivery of other gene(s) using Ad5PTD-based adenoviral vector should follow the same manner as the inventors reported here.

Example 3

The Uses of Ad5PTD-Based Viruses as Oncolytic Agents

Genetically engineered oncolytic adenoviruses have been tested in several clinical cancer trials. Therefore, the present invention also provides Ad5PTD-based oncolytic viruses with enhanced cell killing efficacy caused by higher transduction capacity due to the Tat-PTD modification. Two replication competent Tat-PTD-modified adenoviruses were produced. Ad5PTD(wt) is a wild type adenovirus with Tat-PTD in HVR5, and Ad5PTD(D24) is a Tat-PTD-modified virus with a 24 bp deletion in E1A, which confers selectivity to replication in pRb pathway-deficient cancer cells [16]. In vitro cell killing and viral replication assays were performed. The Ad5PTD(wt) and Ad5PTD(D24) viruses exhibited significantly ($p<0.001$ at 1000 evg/cell) increased killing ability of CAR-negative neuroblastoma and neuroendocrine tumor cells compared to un-modified wild type virus Ad5(wt) (FIG. 4a). Furthermore, Ad5PTD(wt) and Ad5PTD(D24) yielded significantly ($p<0.001$ at day 3) higher numbers of progeny virus compared to Ad5(wt) (FIG. 4b). The increased cell killing and replication are tributes to higher transduction efficacy. Interestingly, Ad5(wt) did replicate in SK-N-SH cells to a certain degree but did not exhibit any killing ability in this cell line, not even at 1000 evg/cell, most likely due to the inability to achieve a high enough transduction level of these cells (FIG. 4a,b), while the Tat-PTD-modified viruses showed both killing and replicating activities (FIG. 4a,b). These results show that the Tat-PTD modification can broaden the viral transduction ability with gain in killing of CAR negative cells and without any loss of oncolytic capacity in CAR-positive cells, as illustrated by killing of Bon cells (FIG. 4c).

The Ad5PTD-based oncolytic adenovirus could also be constructed by using a tumor/tissue specific promoter to control E1a (or other replication essential gene) expression and/or by using microRNA targeting sequence to selectively reduce the E1a (or other replication essential gene) expression in off-target tissues. The tumor cell killing should be increased in the same manner as the inventors reported here.

Example 4

Ad5PTD Based Viruses Overcomes the Fiber-Masking Problem

The adenovirus fiber protein is expressed in huge excess during the viral life cycle [5]. It has been reported that the excess fiber proteins, which are released from the infected cells masks the CAR receptors on uninfected neighboring cells thereby preventing the second round of progeny virus infection [5]. This property hampers the spread of oncolytic virus within tumors. Since the Tat-PTD-modified virus does not need fiber knob-binding to CAR for cell entry, the present invention also provides a method to overcome the fiber-masking problem. GFP expression in cells transduced with Ad5 (GFP) in the presence of soluble fiber was reduced to 20% compared to that in the absence of soluble fiber. However, cells transduced with Ad5PTD(GFP) retained 80% transduction efficacy in the presence of soluble fiber (FIG. 5a). Furthermore, a plaque formation assay to evaluate virus spread during replication was performed. The plaques formed by Ad5PTD(wt) started to be visible at day 3, while the plaques formed by Ad5(wt) started to be visible at day 6. At day 8, the plaques formed by Ad5PTD(wt) was on average 1.6 times larger than the plaques formed by Ad5(wt) (FIG. 5b). A representative data set of the plaques formed by both viruses is shown in FIG. 5c with entire wells shown in the upper panel and 10× magnification of the plaques shown in the lower panel. These results indicate that viruses with the Tat-PTD-modification can overcome the fiber-masking problem to a large degree and thus enhance the second round of infection by progeny virus. Moreover, these results further strengthen the notion that the Tat-PTD-modified virus can enter the cells via a CAR-independent pathway.

Other oncolytic adenoviruses based on Ad5PTD should follow the same manner, in terms of overcoming the fiber-masking problem, as reported here.

Example 5

Tumor Bearing Mice Treatment with Ad5PTD-Based Viruses

To evaluate the oncolytic viruses as therapeutic agents in vivo, SCID/beige mice harboring human neuroblastoma (SK-N-SH), and NMRI-nude mice harboring human neuroendocrine tumors (CNDT2.5) were used. Tumor cells were implanted subcutaneously on the right hind flank. Once established, SK-N-SH tumors on SCID/beige mice were treated with peritumoral injections of Tat-PTD-modified viruses or Ad5(wt) while PBS was used as control. CNDT2.5 tumors on NMRI-nude mice were treated with intratumoral injections of Ad5PTD(D24) while Ad5(mock) and PBS were used as controls. Tumor growth was monitored by caliper measurements.

In the SK-N-SH xenograft model, mice treated with either Ad5PTD(wt) or Ad5PTD(D24) showed a significant ($p<0.001$) suppression of tumor growth (FIG. 6a) and prolonged survival compared to mice treated with Ad5(wt) (FIG. 6b). Interestingly, there was no difference between Ad5(wt)-treated mice and PBS-treated mice, reflecting the lack of Ad5(wt) transduction of SK-N-SH cells. In the CNDT2.5 xenograft model, mice treated with Ad5PTD(D24) showed a significant ($p<0.001$) suppression of tumor growth compared to mice treated with the replication-defective virus Ad5 (mock) or PBS (FIG. 6c). Moreover, mice treated with Ad5PTD(D24) showed a significantly prolonged survival compared to PBS-treated mice and Ad5(mock)-treated mice and in addition, two mice out of six were cured by the Ad5PTD(D24) treatment (FIG. 6d). The better results for Ad5PTD(D24) compared to Ad5(mock) is most likely a combination of the PTD modification, D24 deletion of E1A and the fact that Ad5PTD(D24) replicates while Ad5(mock) does not.

Example 6

The Generation of Ad5PTD-Based Fiber 35 Chimeric Adenovirus

The Ad5PTD-based adenovirus have both CAR-dependent and CAR-independent transduction route. Since CAR is expressed at low levels on some human primary cell types, especially cells of hematopoietic origin, which restricts the Ad5PTD-based viruses to use its fiber 5 mediated, CAR dependent transduction route. Several groups have reported that CD46, the primary receptor for adenovirus serotype 35 (Ad35) is expressed on most human cells throughout the body and shown to be upregulated on tumor cells [17]. To fully utilize the fiber-mediated transduction, we constructed Ad5PTDf35 by switching the adenovirus fiber from serotype 5 to serotype 35 on the Tat-PTD-modified vector. Ad5PTDf35 was generated using recombineering technology in the same manner as the generation of Tat-PTD modification. The als cassette was knocked in to HI-loop of the fiber gene and then replaced by fiber 35 gene, which was amplified from Ad5Easyf35 [18]. This Ad5PTD-based fiber 35 chimeric adenovirus yields higher transduction efficiency on a wide spectrum of human primary cell types including tested T-cells, monocytes, macrophages, dendritic cells, pancreatic islets and exocrine cells, mesenchymal stem cells and cancer initiating cells (FIG. 9). Such vectors could therefore be useful in a functional setting to modify primary cells with the gene of interest as gene delivery vehicles or can be further developed as oncolytic agent for cancer treatment.

Example 7

The Uses of Ad5PTDf3S Modified Primary Human Dendritic Cells (DCs) to Expand Antigen Specific T Cells To demonstrate the beneficial effect of using an Ad5PTDf35-based vector for gene delivery, we constructed Ad5(pp65) and Ad5PTDf35(pp65), which both express the full-length cytomegalovirus (CMV) pp65 transgene. We have previously shown that a population of cytomegalovirus (CMV) pp65495-503-specific T cells can be significantly enriched if T cells from a CMV seropositive, HLA-A2-positive blood donor are stimulated by Ad5(pp65)-transduced autologous dendritic cells (DCs) [19]. However, large amounts of viral vector need to be used. Since monocytes and DCs are far more efficiently transduced with the Ad5PTDf35 (GFP) than the Ad5(GFP) vector (FIG. 8), we argued that we should have the same effect in expanding specific T cells ex vivo by using far less Ad5PTDf35-based vector. We therefore transduced monocytes from four CMV seropositive, HLA-A2-positive blood donors with Ad5(pp65) or Ad5PTDf35 (pp65) at a relatively low dosage (100 evg/cell). The monocytes were then differentiated into DCs [19] and used to stimulate autologous T cells. CMV-pp65-specific T cells were evaluated by HLA-A*0201/pp65459-503 tetramer staining before (pre-stim) and 11 days after stimulation (post-stim). As shown in FIG. 10, the Ad5PTDf35(pp65)/DC stimulation increased the pp65-reactive T cells population for all donors, approximately 50-100 fold, while Ad5(pp65)/DC stimulation only increased the pp65-reactive T cell population 2-8 fold. These data clearly show that Ad5PTDf35(pp65) would be highly efficient for DC modification, to expand T cells ex vivo for adoptive transfer to immunocompromised patients with CMV complications.

Example 8

Ad5PTDf35-Based Oncolytic Virus for Cancer Treatment

As mentioned in example 3, Ad5PTD-based virus could be used as oncolytic agent for cancer treatment. Since the Ad5PTDf35-based virus have better transduction efficiency in most of the tested cells, we believe that this viral vector could improve therapeutic effects for cancer treatment. We generated an oncolytic adenovirus Ad5PTDf35(D24) with 24 bp deletion in the E1a gene to have selective viral replication in cells that have a defective pRb pathway. We found that Ad5PTDf35(D24) could efficiently eradicate cancer cell lines from different origin including neuroendocrine tumor cell line BON (up to 75% killing at MOI 10) and CNDT2.5 (up to 70% killing at MOI 10), neuroblastoma cancer cell line SK-N-FI (up to 75% killing at MOI 10), and melanoma cell line mel526 (up to 70% killing) (FIG. 13). Moreover, we show that tumor growth on a subcutaneous xenograft mice model was significantly delayed after treatment with Ad5PTDf35(D24) compared with control treatment group (FIG. 14a), and the median survival was significantly prolonged after treatment with double modified oncolytic agent Ad5PTDf35(D24) (FIG. 14b).

Example 9

Ad5PTDf35-Based Oncolytic Virus Armed with Therapeutic Gene for Cancer Treatment Oncolytic adenovirus are immunogenic, but are considered to be safe and have been used in several clinical settings [20]. Many reports have suggested that oncolytic viruses could mount tumor-specific immune response which when combined with oncolysis, may enhance the therapeutic efficacy [21]. A strategy by arming adenoviruses with therapeutic genes coding for immune modulating proteins seems to be promising [22]. *Helicobacter pylori* Neutrophil Activating Protein (HP-NAP) was identified to promote neutrophil infiltration to the site of Infection [23]. HP-NAP is a toll-like receptor-2 (TLR-2) agonist and binds to the receptor on neutrophils via its C-terminal region thus stimulating a cascade of intra-cellular events like increase in cytosolic $Ca^{2+}$ concentrations, phosphorylation and assembly of cytosolic subunits of the NADPH oxidases, which leads to the production of reactive oxygen intermediates (ROIs) [23]. HP-NAP is a potent immunomodulator, capable of inducing secretion of the proinflamatory cytokines tumor necrosis factor (TNF)-α and interleukin (IL)-8 and T helper type 1 (Th1) type immune polarization with secretion of IL-12 and IL-23 [24].

Ad5PTDf35(D24-sNAP) is an oncolytic viral agent armed with secretory HP-NAP (FIG. 12a). The HP-NAP coding sequence was codon-optimized for *Homo sapiens* and the synthetic sequence was obtained from GenScript (Piscataway, N.J.) and inserted downstream of the E1aD24 gene. The secretion of HP-NAP was confirmed by western blot assay (FIG. 12b). The biological function of viral expressed HA-NAP was validated and confirmed. We found that secreted HA-NAP could efficiently induce neutrophil migration (FIG. 15a) and binding of HP-NAP to neutrophils activated them to release reactive oxygen species (FIG. 15b).

Ad5PTDf35(D24-sNAP) also showed better cell killing in a majority of the tumor cell lines from different origin. Viability of tumor cell lines transduced in suspension at various multiple of infections (0.01-10 FFU/cell) was measured at day 5. Ad5PTDf35(D24-sNAP) had eradicated 95% of BON (FIG. 13a), 90% of SK-N-FI (FIG. 13b), 75% of CNDT2.5 (FIG. 13c) at MOI 10, and 85% of mel526 cells (FIG. 13d) at MOI 1000. Though not statistically significant, the HP-NAP transgene had an increase in killing efficacy on tumor cells.

In vivo experiments showed that mice treated with oncolytic adenovirus expressing HP-NAP had a syngeneic effect together with viral oncolysis on tumor shrinking and significantly prolonged the survival of tumor bearing mice (FIG. 14). Moreover, viral expressed HP-NAP induced proinflammatory cytokines (TNF-α and MIP2-α) and Th1 type cytokines (IL12/23 p40) (FIG. 15d-f), which can further modulate and mount both cell-mediated and humoral-mediated immune response in tumor microenvironment (FIG. 17).

Histological analysis of tumor tissues isolated from Ad5PTDf35(D24)-treated mice revealed that the tissues contained actively proliferating tumor cells with about 40% tumor necrosis and that the tumor is rather large (FIG. 16a). Whereas the tissues isolated from the two survivors of Ad5PTDf35(D24-sNAP)-treated mice on day 150 revealed that, one of the remaining tissue contained a small tumor nodule (max. 2 mm in size) with more than 60% tumor necrosis (FIG. 16b) and the other tissue contained a small regular structured lymph node surrounded by fat without any sign of tumor growth or metastasis (FIG. 16c). This data suggests that treatment with NAP-armed, PTDf35-based oncolytic adenovirus prolongs survival of tumor-bearing mice.

Example 10

Ad5PTD-Based Oncolytic Virus Controlled by Tumor Selective Promoter

In order to investigate the killing ability of an oncolytic virus controlled by the SCG3 promoter and ASH1 enhancer, we constructed Ad5PTD(ASH1-SCG3-E1A) (FIG. 18) and evaluated it along with Ad5(MOCK) and Ad5PTD(WT). Cell lines were transduced at different evg/cell and relative cell viability was measured after 4 days (FIG. 19). Ad5PTD (ASH1-SCG3-E1A) killed all evaluated neuroblastoma cell lines: SH-SY-5Y, IMR-32, SK-N-DZ, SK-N-AS, Kelly, SK-N-FI and SK-N-SH significantly better than Ad5(MOCK), whereas it had nearly no lytic activity in the non-neuroblastoma cells 1064SK, A549, Mel526 and Hela, not significantly different from Ad5(MOCK). The Ad5PTD(WT), which was used as a positive control showed killing ability in all cell lines without any selectivity. These results suggests that Ad5PTD(ASH1-SCG3-E1A) possesses efficient and selective killing of neuroblastoma cells.

We next wanted to examine the efficacy of Ad5PTD (ASH1-SCG3-E1A) to control tumor growth in vivo. SK-N-FI cells were injected subcutaneously in nude mice and established tumors were on day 7 treated with peritumoral injection of either Ad5PTD(MOCK) or Ad5PTD(ASH1-SCG3-E1A). The tumors were treated again on day 13 and day 18. Tumor size was monitored through caliper measurements. Mice treated with Ad5PTD(ASH1-SCG3-E1A) exhibited suppression of tumor growth compared to mice treated with Ad5PTD(MOCK). At day 47 (FIG. 20A, vertical line), two out of the six Ad5PTD(ASH1-SCG3-E1A)-treated mice had been sacrificed and the tumor sizes of three of the remaining mice were around 100 mm$^3$ and one around 400 mm$^3$ while five out of the six Ad5PTD(MOCK)-treated mice had been sacrificed and the tumor size of the remaining mouse was 800 mm$^3$ (FIG. 20B, vertical line). The last mouse in the Ad5PTD(MOCK) treated group had to be sacrificed on day 54, while four out of six mice from the Ad5PTD(ASH1-SCG3-E1A) treated group were alive at 60 days when the experiment was terminated. All mice had tumors at the time of termination but only one out of the four mice had a growing tumor.

Compared as two groups of mice, Ad5PTD(ASH1-SCG3-E1A)-treated mice had statistically significant smaller tumors than Ad5PTD(MOCK)-treated mice (FIG. 20C). Furthermore, mice treated with Ad5PTD(ASH1-SCG3-E1A) showed a significantly prolonged survival compared to Ad5PTD(MOCK)-treated mice (FIG. 20D). In order to evaluate the viral replication in vivo and tumor histology, three mice from Ad5PTD(MOCK)-treatment or Ad5PTD(ASH1-SCG3-E1A)-treatment group were sacrificed 3 days after the last treatment (day 21). Tumor and liver were analyzed by qPCR to detect virus replication. Ad5PTD(ASH1-SCG3-E1A) virus replicates better in tumor as compared to Ad5PTD (MOCK) virus (FIG. 20E). On the other hand we could detect very low levels of both the viruses in the liver, suggesting that even though the Ad5PTD(ASH1-SCG3-E1A) virus replicates in the tumor, there is very little leakage in to the circulation (FIG. 20F). Necrosis of the tumor was viewed by H&E staining and quantified in a blinded manner by an experienced pathologist (FIG. 20G). Tumors treated with Ad5PTD (ASH1-SCG3-E1A) had significantly higher amount necrotic areas compared with mock virus treated tumor. The hexon staining is co-localized within the nuclei depicting the progeny viral particles. This suggests that the necrosis is due to viral replication inside tumor cells (FIG. 20H).

Example 11

Ad5PTDf35-Based Viral Vector for Gene Delivery and Cancer Treatment

An Ad5PTDf35-based non-replicative vector carrying the gene for mouse CD40L was engineered, Ad5PTDf35 (mCD40L) along with a control vector with transgene, Ad5PTDf35(Mock). Standard Ad5-based non-replicative vectors either carrying the mouse CD40L transgene or without transgene was also engineered. Schematic illustrations of the AdmCD40L and Ad5PTDf35(mCD40L) vectors are shown in FIG. 21. Mouse cells were transduced with these vectors and CD40L expression was then analyzed by flow cytometry. The expression of CD40L was significantly improved for the Ad5PTDf35-based virus in mouse bladder cancer cells (MB49), mouse dendritic cells (D1) and mouse splenocytes (FIG. 22A-D) when compared with Ad5-based viral vector. The two vectors worked equally well for mouse melanoma cells (B16-F10).

Animal experiments were carried out where the AdmCD40L vector was compared with the Ad5PTDf35 (mCD40L) vector in regard to tumor growth and immune cells infiltrating the tumor. Three intratumoral treatments were given with three days apart at 5×10$^9$ evg/injection. The Ad5PTDf35(mCD40L) vector was able to delay tumor growth (FIG. 23A). Survival of the animals were prolonged in the groups treated with the Ad5PTDf35(mCD40L) vector and its control vector, in comparison to the groups treated with AdmCD40L and AdMock (FIG. 23B). Four animals were sacrificed 24 hours after the last treatment and the tumors were harvested, digested and analyzed for infiltration of macrophages. The number of macrophages was equal in all groups. However, there is an increase in M1 and a decrease in M2 macrophages in the tumors that were treated with the Ad5PTDf35-based vector, in comparison with the wild type based AdmCD40L treated tumors (FIG. 23C). M1 macrophages also known as classically activated macrophages are effector immune cells that are aggressive against microbes and can engulf and digest affected cells much more readily, and they also produce many lymphokines while M2 macrophages also known as tumor-infiltrating macrophages are know to be immune-suppressive and thereby support tumor growth.

Local administration of an adenoviral vector carrying the CD40L transgene enables the vector to infect any cell it encounters, including dendritic cells. Therefore the ability of the mouse dendritic cell D1, modified to express CD40L, to present antigen to T cells was investigated in an antigen presentation assay. Both transduced and untransduced D1 cells were loaded with the short H-2D$^b$ restricted hgp100 peptide at a concentration of 0.025 ng/mL and allowed to interact with CFSE stained splenocytes from PmeI mice. T cells from PmeI mice carry a TCR specific for hgp100 in H-2 D$^b$. Proliferation of T cells was determined by flow cytometry 72 hours after co-culture. Proliferation of T cells encountering Ad5PTDf35(mCD40L)-transduced D1 cells increased significantly compared to T cells encountering AdmCD40L-transduced D1 cells (FIG. 24A). Supernatant from the co-cultures were collected and analyzed for IFN-γ secretion and it was found that the concentration increased significantly in the co-cultures where D1 cells had been transduced with Ad5PTDf35(mCD40L) (FIG. 24B). An antigen presentation assay was also performed in vivo, where splenocytes from a PmeI mouse (C57/BL6 background but Thy1.1$^+$) were injected intravenously into a wild-type immunocompetent C57/BL6 mice (Thy1.1$^-$), followed by an intravenously injection of hgp100 peptide-loaded, vector-transduced D1 cells 24 hours later. Four days later the spleen and the inguinal lymph nodes were collected and the percentage of hgp100-specific T cells was determined in the CD8$^+$ T cell population. In both spleen and lymph nodes the highest percentage of hgp100-specific T cells were found in the animals who had been injected with Ad5PTDf35(mCD40L)-transduced D1 cells (FIG. 24C). The improved antigen presentation can be explained by improved CD40L augmentation as well as the increased IL-12 secretion by D1 cells (FIG. 24D).

Example 12

Ad5PTD-Based Oncolytic Viruses for Cancer Treatment in Combination with Chemotherapy Drugs A cisplatin-insensitive clone of the SK-N-FI neuroblastoma cell line and doxorubicin-, etoposide- and vincristine-insensitive clones of SH-SY-SY were established and treated with viruses at different evg/cell or drugs at various concentrations. The relative cell viability was analyzed by MTS assay. Ad5PTD(ASH1-SCG3-E1A) killed cisplatin-sensitive and insensitive SK-N-FI cells with the same efficacy (IC50 of 6 evg/cell), while 12-fold more cisplatin was needed to kill cisplatin-insensitive SK-N-FI cells (IC50 of 100 μM) compared to cisplatin-sensitive SK-N-FI cells (IC50 of 8 μM), (FIG. 25A). Ad5PTD(WT) also killed cisplatin-sensitive and insensitive SK-N-FI with the same efficacy (FIG. 25A). Similar results were observed for virus killing of etoposide-insensitive SH-SY-5Y (FIG. 25B) and doxorubicin-insensitive SH-SY-SY (FIG. 25C) while vincristine-insensitive SH-SY-SY proved difficult to kill both with Ad5PTD(ASH1-SCG3-E1A) and Ad5PTD(WT), (FIG. 25D).

In another experimental setting, PTD-based oncolytic adenovirus Ad5PTD(i/CgA-E1a-miR122T6) was evaluated for the killing efficacy of BON, NCI-H727 and QGP-1 cell lines in vitro in combination with different concentration of cyclophosphamide (10 μg/mL or 200 μg/mL). We do not see any drug-related inhibition of adenovirus killing efficacy (FIG. 25E). These results further demonstrated our PTD-based oncolytic virus could be used in combination with chemotherapy drugs.

REFERENCE

1. Essand, M., et al., *Oncolytic Viruses for the Treatment of Neuroendocrine Tumors*. Horm Metab Res, 2011. 43(12): p. 877-83.
2. Leja, J., et al., *Double-detargeted oncolytic adenovirus shows replication arrest in liver cells and retains neuroendocrine cell killing ability*. PLoS One, 2010. 5(1): p. e8916.
3. Terao, S., et al., *Improved gene transfer into renal carcinoma cells using adenovirus vector containing RGD motif*. Anticancer Res, 2009. 29(8): p. 2997-3001.
4. Wang, H., et al., *Desmoglein 2 is a receptor for adenovirus serotypes 3, 7, 11 and 14*. Nat Med, 2011. 17(1): p. 96-104.
5. Rebetz, J., et al., *Fiber mediated receptor masking in non-infected bystander cells restricts adenovirus cell killing effect but promotes adenovirus host co-existence*. PLoS One, 2009. 4(12): p. e8484.
6. Vives, E., P. Brodin, and B. Lebleu, *A truncated HIV-1 Tat protein basic domain rapidly translocates through the plasma membrane and accumulates in the cell nucleus*. J Biol Chem, 1997. 272(25): p. 16010-7.
7. Sawant, R. and V. Torchilin, *Intracellular transduction using cell-penetrating peptides*. Mol Biosyst, 2010. 6(4): p. 628-40.
8. Cheng, W. S., et al., *An oncolytic conditionally replicating adenovirus for hormone-dependent and hormone-independent prostate cancer*. Cancer gene therapy, 2006. 13(1): p. 13-20.
9. Danielsson, A., et al., *Increased therapeutic efficacy of the prostate-specific oncolytic adenovirus Ad[I/PPT-E1A] by reduction of the insulator size and introduction of the full-length E3 region*. Cancer gene therapy, 2008. 15(4): p. 203-13.
10. Leja, J., et al., *A novel chromogranin—A promoter-driven oncolytic adenovirus for midgut carcinoid therapy*. Clin Cancer Res, 2007. 13(8): p. 2455-62.
11. Eto, Y., et al., *Transduction of adenovirus vectors modified with cell-penetrating peptides*. Peptides, 2009. 30(8): p. 1548-52.
12. Kurachi, S., et al., *Fiber-modified adenovirus vectors containing the TAT peptide derived from HIV-1 in the fiber knob have efficient gene transfer activity*. Gene Ther, 2007. 14(15): p. 1160-5.
13. Leja, J., et al., *A novel chromogranin—A promoter-driven oncolytic adenovirus for midgut carcinoid therapy*. Clinical cancer research: an official journal of the American Association for Cancer Research, 2007. 13(8): p. 2455-62.
14. Stanton, R. J., et al., *Re-engineering adenovirus vector systems to enable high-throughput analyses of gene function*. Biotechniques, 2008. 45(6): p. 659-62, 664-8.
15. Leja, J., et al., *Oncolytic adenovirus modified with somatostatin motifs for selective infection of neuroendocrine tumor cells*. Gene Ther, 2011. 18(11): p. 1052-62.
16. Fueyo, J., et al., *A mutant oncolytic adenovirus targeting the Rb pathway produces anti-glioma effect in vivo*. Oncogene, 2000. 19(1): p. 2-12.
17. Ni Choileain, S, and A. L. Astier, *CD46 processing: A means of expression*. Immunobiology, 2012. 217(2): p. 169-75.
18. Nilsson, M., et al., *Development of an adenoviral vector system with adenovirus serotype 35 tropism; efficient transient gene transfer into primary malignant hematopoietic cells*. J Gene Med, 2004. 6(6): p. 631-41.
19. Carlsson, B., et al., *Ex vivo stimulation of cytomegalovirus (CMV)-specific T cells using CMV pp65-modified dendritic cells as stimulators*. Br J Haematol, 2003. 121(3): p. 428-38.
20. Yu, W. and H. Fang, *Clinical trials with oncolytic adenovirus in China*. Curr Cancer Drug Targets, 2007. 7(2): p. 141-8.

21. QJao, J., et al., *Purging metastases in lymphoid organs using a combination of antigen-nonspecific adoptive T cell therapy, oncolytic virotherapy and immunotherapy*. Nat Med, 2008. 14(1): p. 37-44.
22. Lee, Y. S., et al., *Enhanced antitumor effect of oncolytic adenovirus expressing interleukin-12 and B7-1 in an immunocompetent murine model*. Clin Cancer Res, 2006. 12(19): p. 5859-68.
23. Satin, B., et al., *The neutrophil-activating protein (HP-NAP) of Helicobacter pylori is a protective antigen and a major virulence factor*. J Exp Med, 2000. 191(9): p. 1467-76.
24. Amedei, A., et al., *The neutrophil-activating protein of Helicobacter pylori promotes Th1 immune responses*. J Cin Invest, 2006. 116(4): p. 1092-101.

The invention claimed is:

1. An adenovirus, comprising at least one of (i) an adenovirus hexon protein which is modified to comprise at least one protein transduction domain of the Tat protein from Human Immunodeficiency Virus (HIV) and (ii) a recombinant nucleic acid molecule encoding said modified adenovirus hexon protein, wherein said modified adenovirus hexon protein comprises the amino acid sequence of SEQ ID NO:2 inserted into hypervariable region 5 of the adenovirus hexon protein.

2. The adenovirus according to claim 1, wherein said modified adenovirus hexon protein comprises the amino acid sequence according to SEQ ID NO:3.

3. The adenovirus of claim 1, wherein the adenovirus is selected from the group consisting of serotype-2 (Ad2), -3 (Ad3), -7(Ad7), -11 (Ad11), -17 (Ad17), -35 (Ad35), -41 (Ad41), -48 (Ad48) and their derivatives.

4. The adenovirus of claim 1, wherein the adenovirus is an adenovirus serotype 5 comprising a fiber and/or fiber knob of other adenovirus serotypes, in place of the adenovirus serotype 5 fiber and/or fiber knob.

5. The adenovirus of claim 4, comprising the fiber and/or fiber knob of adenovirus serotypes selected from serotypes Ad2, Ad3, Ad7, Ad11, Ad17, Ad35, Ad41 and Ad48.

6. The adenovirus of claim 1, wherein the adenovirus is operatively modified by a heterologous nucleotide sequence, which codes for the amino acid sequence of SEQ ID NO:2 inserted into hypervariable region 5 of the adenovirus hexon protein.

7. The adenovirus of claim 1, wherein E1 and/or E3 and/or E4 regions of the adenovirus are deleted.

8. The adenovirus of claim 1, wherein the adenovirus is of serotype 5 and wherein said adenovirus hexon protein is derived from serotype Ad2, Ad3, Ad35, Ad11, Ad17, Ad41, Ad48 and their derivatives.

9. The adenovirus of claim 1, further comprising at least one heterologous nucleic acid molecule in addition to any recombinant nucleic acid molecule encoding an adenovirus hexon protein modified to comprise the amino acid sequence of SEQ ID NO:2 inserted into hypervariable region 5 of the adenovirus hexon protein.

10. The adenovirus of claim 1, wherein an E1a gene of the adenovirus is controlled by a tissue-specific promoter and/or a tumor-specific promoter, and/or is a mutated E1a gene.

11. The adenovirus of claim 1, wherein the adenovirus comprises one or more therapeutic genes.

12. The adenovirus of claim 1, wherein an E1a gene is under control of a tissue-specific or tumor-specific promoter, and comprises one or more therapeutic genes.

13. The adenovirus of claim 12, wherein the tissue specific promoter is selected from the group consisting of the prostate cell-specific PPT promoter, the neuroendocrine cell-specific CgA promoter, and the neuroblastoma-specific SCG3, SCG2, NESP-55 promoters; and the tumor-specific promoter is selected from the group consisting of the hTERT, Cox-2, survivin and E2F-1 promoters.

14. The adenovirus of claim 11, wherein the therapeutic genes are selected from the group consisting of the genes encoding CD40L, HRG, HP-NAP, GM-CSF, HSV-TK and cytosine deaminase, and codon-optimized versions thereof.

15. A pharmaceutical composition comprising the adenovirus of claim 1, and optionally pharmaceutically acceptable buffers, carriers and excipients.

16. The pharmaceutical composition of claim 15, wherein the composition is derived/generated by the said adenovirus.

17. A method of treating cancer in a subject, comprising administrating to the subject a therapeutically effective amount of adenovirus according to claim 1.

18. A method according to claim 17, further comprising additional treatment of cancer.

19. A method according to claim 18, wherein said additional treatment of cancer is selected from surgery, traditional Chinese medicine, acupuncture, chemotherapy, radiotherapy, therapeutic antibodies.

20. A method of delivering a heterologous nucleic acid molecule to a mammalian cell, comprising bringing said mammalian cell into contact with an adenovirus according to claim 1 under conditions allowing delivery of said heterologous nucleic acid molecule to said mammalian cell.

21. A method of treating, or ameliorating a disease or condition in a subject, comprising delivering a heterologous nucleic acid molecule to at least one cell of said subject by bringing said cell into contact with an adenovirus according to claim 1 under conditions allowing delivery of said heterologous nucleic acid molecule to said cell, wherein said heterologous nucleic acid molecule is effective to at least in part treat or ameliorate the disease or condition.

22. A method according to claim 21, wherein said disease or condition is a cancer.

23. A method according to claim 21, wherein said disease or condition is influenced by a genetic factor and said heterologous nucleic acid molecule is effective to at least in part counter or compensate for said genetic factor.

24. The adenovirus according to claim 10, wherein the mutated E1a gene is E1a-delta24.

* * * * *

SEQUENCE LISTING

```
<160> NUMBER OF SEQ ID NOS: 3

<210> SEQ ID NO 1
<211> LENGTH: 11
<212> TYPE: PRT
<213> ORGANISM: Human immunodeficiency virus type 1

<400> SEQUENCE: 1

Tyr Gly Arg Lys Lys Arg Arg Gln Arg Arg Arg
1               5                   10

<210> SEQ ID NO 2
<211> LENGTH: 27
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Protein transduction domain with linker
      sequences

<400> SEQUENCE: 2

Ala Gly Gly Gly Ala Gly Gly Gly Tyr Gly Arg Lys Lys Arg Gln
1               5                   10                  15

Arg Arg Arg Gly Gly Gly Ala Gly Gly Gly Ala
            20                  25

<210> SEQ ID NO 3
<211> LENGTH: 969
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Tat-PTD modified adenovirus 5 hexon
<220> FEATURE:
<221> NAME/KEY: MISC_FEATURE
<222> LOCATION: (271)..(278)
<223> OTHER INFORMATION: Linker
<220> FEATURE:
<221> NAME/KEY: MISC_FEATURE
<222> LOCATION: (278)..(289)
<223> OTHER INFORMATION: Tat-PTD
<220> FEATURE:
<221> NAME/KEY: MISC_FEATURE
<222> LOCATION: (290)..(297)
<223> OTHER INFORMATION: Linker

<400> SEQUENCE: 3

Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
                20                  25                  30

Arg Ala Thr Glu Thr Tyr Phe Ser Leu Asn Asn Lys Phe Arg Asn Pro
            35                  40                  45

Thr Val Ala Pro Thr His Asp Val Thr Thr Asp Arg Ser Gln Arg Leu
```

```
            50                  55                  60
Thr Leu Arg Phe Ile Pro Val Asp Arg Glu Asp Thr Ala Tyr Ser Tyr
 65                  70                  75                  80

Lys Ala Arg Phe Thr Leu Ala Val Gly Asp Asn Arg Val Leu Asp Met
                 85                  90                  95

Ala Ser Thr Tyr Phe Asp Ile Arg Gly Val Leu Asp Arg Gly Pro Thr
                100                 105                 110

Phe Lys Pro Tyr Ser Gly Thr Ala Tyr Asn Ala Leu Ala Pro Lys Gly
            115                 120                 125

Ala Pro Asn Pro Cys Glu Trp Asp Glu Ala Ala Thr Ala Leu Glu Ile
130                 135                 140

Asn Leu Glu Glu Glu Asp Asp Asn Glu Asp Glu Val Asp Glu Gln
145                 150                 155                 160

Ala Glu Gln Gln Lys Thr His Val Phe Gly Gln Ala Pro Tyr Ser Gly
                165                 170                 175

Ile Asn Ile Thr Lys Glu Gly Ile Gln Ile Gly Val Glu Gly Gln Thr
                180                 185                 190

Pro Lys Tyr Ala Asp Lys Thr Phe Gln Pro Glu Pro Gln Ile Gly Glu
            195                 200                 205

Ser Gln Trp Tyr Glu Thr Glu Ile Asn His Ala Ala Gly Arg Val Leu
210                 215                 220

Lys Lys Thr Thr Pro Met Lys Pro Cys Tyr Gly Ser Tyr Ala Lys Pro
225                 230                 235                 240

Thr Asn Glu Asn Gly Gly Gln Gly Ile Leu Val Lys Gln Gln Asn Gly
                245                 250                 255

Lys Leu Glu Ser Gln Val Glu Met Gln Phe Phe Ser Thr Thr Ala Gly
            260                 265                 270

Gly Gly Ala Gly Gly Gly Tyr Gly Arg Lys Lys Arg Gln Arg Arg
            275                 280                 285

Arg Gly Gly Gly Ala Gly Gly Ala Thr Pro Lys Val Val Leu Tyr
            290                 295                 300

Ser Glu Asp Val Asp Ile Glu Thr Pro Asp Thr His Ile Ser Tyr Met
305                 310                 315                 320

Pro Thr Ile Lys Glu Gly Asn Ser Arg Glu Leu Met Gly Gln Gln Ser
                325                 330                 335

Met Pro Asn Arg Pro Asn Tyr Ile Ala Phe Arg Asp Asn Phe Ile Gly
                340                 345                 350

Leu Met Tyr Tyr Asn Ser Thr Gly Asn Met Gly Val Leu Ala Gly Gln
            355                 360                 365

Ala Ser Gln Leu Asn Ala Val Val Asp Leu Gln Asp Arg Asn Thr Glu
370                 375                 380

Leu Ser Tyr Gln Leu Leu Leu Asp Ser Ile Gly Asp Arg Thr Arg Tyr
385                 390                 395                 400

Phe Ser Met Trp Asn Gln Ala Val Asp Ser Tyr Asp Pro Asp Val Arg
                405                 410                 415

Ile Ile Glu Asn His Gly Thr Glu Asp Glu Leu Pro Asn Tyr Cys Phe
                420                 425                 430

Pro Leu Gly Gly Val Ile Asn Thr Glu Thr Leu Thr Lys Val Lys Pro
            435                 440                 445

Lys Thr Gly Gln Glu Asn Gly Trp Glu Lys Asp Ala Thr Glu Phe Ser
            450                 455                 460

Asp Lys Asn Glu Ile Arg Val Gly Asn Asn Phe Ala Met Glu Ile Asn
465                 470                 475                 480
```

```
Leu Asn Ala Asn Leu Trp Arg Asn Phe Leu Tyr Ser Asn Ile Ala Leu
                485                 490                 495

Tyr Leu Pro Asp Lys Leu Lys Tyr Ser Pro Ser Asn Val Lys Ile Ser
            500                 505                 510

Asp Asn Pro Asn Thr Tyr Asp Tyr Met Asn Lys Arg Val Val Ala Pro
            515                 520                 525

Gly Leu Val Asp Cys Tyr Ile Asn Leu Gly Ala Arg Trp Ser Leu Asp
            530                 535                 540

Tyr Met Asp Asn Val Asn Pro Phe Asn His His Arg Asn Ala Gly Leu
545                 550                 555                 560

Arg Tyr Arg Ser Met Leu Leu Gly Asn Gly Arg Tyr Val Pro Phe His
                565                 570                 575

Ile Gln Val Pro Gln Lys Phe Phe Ala Ile Lys Asn Leu Leu Leu Leu
                580                 585                 590

Pro Gly Ser Tyr Thr Tyr Glu Trp Asn Phe Arg Lys Asp Val Asn Met
                595                 600                 605

Val Leu Gln Ser Ser Leu Gly Asn Asp Leu Arg Val Asp Gly Ala Ser
            610                 615                 620

Ile Lys Phe Asp Ser Ile Cys Leu Tyr Ala Thr Phe Pro Met Ala
625                 630                 635                 640

His Asn Thr Ala Ser Thr Leu Glu Ala Met Leu Arg Asn Asp Thr Asn
                645                 650                 655

Asp Gln Ser Phe Asn Asp Tyr Leu Ser Ala Ala Asn Met Leu Tyr Pro
                660                 665                 670

Ile Pro Ala Asn Ala Thr Asn Val Pro Ile Ser Ile Pro Ser Arg Asn
                675                 680                 685

Trp Ala Ala Phe Arg Gly Trp Ala Phe Thr Arg Leu Lys Thr Lys Glu
                690                 695                 700

Thr Pro Ser Leu Gly Ser Gly Tyr Asp Pro Tyr Tyr Thr Tyr Ser Gly
705                 710                 715                 720

Ser Ile Pro Tyr Leu Asp Gly Thr Phe Tyr Leu Asn His Thr Phe Lys
                725                 730                 735

Lys Val Ala Ile Thr Phe Asp Ser Ser Val Ser Trp Pro Gly Asn Asp
                740                 745                 750

Arg Leu Leu Thr Pro Asn Glu Phe Glu Ile Lys Arg Ser Val Asp Gly
                755                 760                 765

Glu Gly Tyr Asn Val Ala Gln Cys Asn Met Thr Lys Asp Trp Phe Leu
                770                 775                 780

Val Gln Met Leu Ala Asn Tyr Asn Ile Gly Tyr Gln Gly Phe Tyr Ile
785                 790                 795                 800

Pro Glu Ser Tyr Lys Asp Arg Met Tyr Ser Phe Phe Arg Asn Phe Gln
                805                 810                 815

Pro Met Ser Arg Gln Val Val Asp Asp Thr Lys Tyr Lys Asp Tyr Gln
                820                 825                 830

Gln Val Gly Ile Leu His Gln His Asn Asn Ser Gly Phe Val Gly Tyr
            835                 840                 845

Leu Ala Pro Thr Met Arg Glu Gly Gln Ala Tyr Pro Ala Asn Phe Pro
850                 855                 860

Tyr Pro Leu Ile Gly Lys Thr Ala Val Asp Ser Ile Thr Gln Lys Lys
865                 870                 875                 880

Phe Leu Cys Asp Arg Thr Leu Trp Arg Ile Pro Phe Ser Ser Asn Phe
                885                 890                 895
```

```
Met Ser Met Gly Ala Leu Thr Asp Leu Gly Gln Asn Leu Leu Tyr Ala
            900                 905                 910

Asn Ser Ala His Ala Leu Asp Met Thr Phe Glu Val Asp Pro Met Asp
        915                 920                 925

Glu Pro Thr Leu Leu Tyr Val Leu Phe Glu Val Phe Asp Val Val Arg
    930                 935                 940

Val His Gln Pro His Arg Gly Val Ile Glu Thr Val Tyr Leu Arg Thr
945                 950                 955                 960

Pro Phe Ser Ala Gly Asn Ala Thr Thr
                965
```